US009895501B2

(12) United States Patent
Von Schuckmann et al.

(10) Patent No.: US 9,895,501 B2
(45) Date of Patent: Feb. 20, 2018

(54) METERING DEVICE FOR THE INHALATION OF A PULVERULENT SUBSTANCE

(71) Applicant: SANOFI SA, Meyrin (CH)

(72) Inventors: Alfred Von Schuckmann, Kevelaer (DE); Yorick Kamlag, Pähl (DE); Stefan Mayer, Freiburg (DE); Dennis Sandell, München (DE)

(73) Assignee: Sanofi-Aventis Deutschland GmbH, Frankfurst am Main (DE)

( * ) Notice: Subject to any disclaimer, the term of this patent is extended or adjusted under 35 U.S.C. 154(b) by 915 days.

(21) Appl. No.: 14/021,915

(22) Filed: Sep. 9, 2013

(65) Prior Publication Data

US 2014/0076313 A1    Mar. 20, 2014

Related U.S. Application Data

(63) Continuation of application No. 12/744,366, filed as application No. PCT/EP2008/064661 on Oct. 29, 2008, now Pat. No. 8,573,204.

(30) Foreign Application Priority Data

Nov. 22, 2007  (DE) .......................... 10 2007 056 263

(51) Int. Cl.
    *A61M 15/00*    (2006.01)
(52) U.S. Cl.
    CPC .... *A61M 15/0065* (2013.01); *A61M 15/0006* (2014.02); *A61M 15/0025* (2014.02);
    (Continued)
(58) Field of Classification Search
    CPC .......... A61M 15/0065; A61M 15/0066; A61M 15/0001; A61M 15/0005; A61M 15/0006;
    (Continued)

(56) References Cited

U.S. PATENT DOCUMENTS

| 5,263,475 A | 11/1993 | Altermatt et al. |
| 5,347,999 A | 9/1994 | Poss et al. |

(Continued)

FOREIGN PATENT DOCUMENTS

| AU | 62916 C2 | 1/2004 |
| CA | 2576074 A1 | 3/2006 |

(Continued)

OTHER PUBLICATIONS

English Translation Abstract of JP 2006-502752 dated Mar. 9, 2015.

(Continued)

*Primary Examiner* — Todd J Scherbel
*Assistant Examiner* — Elliot S Ruddie
(74) *Attorney, Agent, or Firm* — McDonnell Boehnen Hulbert & Berghoff LLP

(57) ABSTRACT

A metering device activated by a user induced airstream for an inhalation of a medicinal substance. The device includes: a closure cap; a piston; a mouthpiece; and an annular chamber disposed upstream of the mouthpiece. A storage chamber stores the substance which can be moved out of the storage chamber when the closure cap is removed. A metering rod for removing the medicinal substance out of the storage chamber into an emptying-standby position. In the emptying-standby position, the metering chamber is closed by the piston. The piston is displaceable by airstream into an emptying-release position. In the emptying-release position, a metering chamber is released and the substance removed by the suction airstream. The metering device includes an outer cylinder which accommodates an inner cylinder.

6 Claims, 21 Drawing Sheets

(52) U.S. Cl.
CPC .... *A61M 15/0086* (2013.01); *A61M 15/0091* (2013.01); *A61M 2202/062* (2013.01); *A61M 2202/064* (2013.01); *A61M 2206/16* (2013.01)

(58) Field of Classification Search
CPC ............ A61M 15/002; A61M 15/0021; A61M 15/0025; A61M 15/0086; A61M 15/0088; A61M 15/0091; A61M 15/0093; A61M 15/0095; A61M 15/0096; A61M 2202/062; A61M 2202/064; A61M 2206/16
USPC ............. 128/200.24, 203.12, 203.13, 203.15
See application file for complete search history.

(56) References Cited

U.S. PATENT DOCUMENTS

| | | | |
|---|---|---|---|
| 5,429,122 A * | 7/1995 | Zanen | A61M 15/0065 128/200.22 |
| 5,617,845 A | 4/1997 | Poss et al. | |
| 5,673,685 A | 10/1997 | Heide et al. | |
| 5,840,279 A | 11/1998 | Narodylo et al. | |
| 5,869,853 A | 2/1999 | Yu | |
| 6,212,959 B1 | 4/2001 | Perkins | |
| 6,606,992 B1 | 8/2003 | Schuler et al. | |
| 7,658,721 B2 | 2/2010 | Steiner et al. | |
| 7,845,346 B2 | 12/2010 | Langord et al. | |
| 8,210,170 B2 * | 7/2012 | von Schuckmann | A61M 15/0065 128/200.24 |
| 8,261,737 B2 | 9/2012 | von Schuckmann | |
| 8,327,842 B2 | 12/2012 | von Schuckmann | |
| 8,701,660 B2 | 4/2014 | Von Schuckmann | |
| 2004/0035421 A1 | 2/2004 | Schuckmann | |
| 2007/0246042 A1 * | 10/2007 | Purkins | A61M 15/0065 128/200.14 |
| 2007/0289593 A1 * | 12/2007 | von Schuckmann | A61M 15/0065 128/203.15 |
| 2009/0064997 A1 | 3/2009 | Li | |
| 2009/0260626 A1 | 10/2009 | Von Schuckmann | |
| 2010/0175696 A1 * | 7/2010 | Ishizeki | A61M 15/0028 128/203.15 |
| 2010/0258118 A1 | 10/2010 | Morton | |
| 2013/0112199 A1 * | 5/2013 | Von Schuckmann | A61M 15/0065 128/203.15 |

FOREIGN PATENT DOCUMENTS

| | | | |
|---|---|---|---|
| CA | 2706569 A1 | 5/2009 | |
| CA | 2706572 A1 | 5/2009 | |
| CN | 101048187 A | 10/2007 | |
| DE | 102006029753 A1 | 9/2007 | |
| EP | 0505321 A2 | 9/1992 | |
| JP | 2001520088 A | 10/2001 | |
| JP | 2005103835 A | 4/2005 | |
| JP | 2006502752 A | 1/2006 | |
| JP | 2006312086 A | 11/2006 | |
| JP | 2008510543 A | 4/2008 | |
| RU | 2091088 C1 | 9/1997 | |
| RU | 2095091 C1 | 11/1997 | |
| WO | 9106333 A1 | 5/1991 | |
| WO | 97/20589 A1 | 6/1997 | |
| WO | 9920331 A1 | 4/1999 | |
| WO | 0226299 A1 | 4/2002 | |
| WO | 2004033009 A1 | 4/2004 | |
| WO | 2006021546 A1 | 3/2006 | |
| WO | WO 2006021546 A1 * | 3/2006 | A61M 15/0065 |
| WO | 2007009872 A1 | 1/2007 | |
| WO | 2007104694 A1 | 9/2007 | |

OTHER PUBLICATIONS

Notice of Reason for Rejection issued in Chinese Patent Application No. 2014-014674 dated Jan. 1, 2015.
English Translation of the Examination Report issued in Taiwanese Patent Application No. 0516/10321314690 dated Sep. 23, 2014.

* cited by examiner

METERING DEVICE FOR THE INHALATION OF A PULVERULENT SUBSTANCE

CROSS REFERENCE TO RELATED APPLICATIONS

The present application is a continuation application of U.S. patent application Ser. No. 12/744,366, filed Aug. 18, 2010 which is a 35 U.S.C. 371 National Application of PCT/EP2008/064661 filed Oct. 29, 2008, which claims priority to German Patent Application No. 102007056263.4 filed Nov. 22, 2007 the entire contents of which are incorporated entirely herein by reference.

The invention relates to a metering device which can be activated by the user's suction airstream and is intended for the inhalation of a pulverulent substance, in particular a medicinal substance, according to the preamble of the main claim.

A metering device of the type in question is known from WO 2006/021546 A1. The quantity of substance separated off in the metering chamber is moved into a closed emptying-standby position. As a result of a user breathing in, a piston moves and opens the metering chamber. Thereafter, the latter is connected to an air-flow path for clearing the separated-off quantity of substance out of the metering chamber and transferring it into the airstream which is to be sucked in.

In view of this known prior art, it may be considered to be a technical problem of the invention to develop in an advantageous manner a metering device of the type in question in respect of optimum air channeling. WO 02/26299 has already proposed to use the suction airstream both for displacing a metering rod and for conveying the substance through the mouthpiece. These solutions, however, can only be used with the metering device in the upright position, that is to say they cannot be used, in practice, when the user is lying in bed. There is also a risk of the inhaler-substance mixture separating.

The problem of optimum air channeling is solved substantially by the subject matter of Claim 1. Two airstreams meet in an annular chamber, one of the airstreams initially opening the metering chamber and then coming into contact with the other airstream in the annular chamber. The configuration selected for the piston means that only a relatively low mass needs to be shifted when the piston is displaced, but a large-area engagement surface is provided, and this makes it easier for the piston to be moved out of the emptying-standby position into the emptying-release position by means of the user's suction airstream. Accordingly, only a relatively low level of suction airstream energy is required in order to release the metering chamber. Furthermore, the narrow construction of the piston makes it possible to achieve increased levels of air energy during inhalation.

In an advantageous development, it is provided that, in its upper end position, the upper periphery of the piston engages in front of an annular wall, which belongs to an annular chamber, and preferably the ceiling of the latter has peripherally extending, projecting wings which leave intermediate spaces between them. Disposed downstream of the same is a ceiling portion which constitutes an oblique deflecting wall with concentrating action. Further preferably, the piston, which has air flowing around it during inhalation, i.e. during suction-air activation by the user, releases the path to the annular chamber in the upper position, i.e. in the emptying-release position of the metering chamber, with sealing engagement against the annular wall of the annular chamber. The annular chamber acts in the manner of a vortex chamber, in which the powder which is to be inhaled is distributed optimally in the suction air. The powder which is to be inhaled consists, for example, of a basic body, such as lactose, which can be transported by a suction stream and is suitable as a carrier for fine micronized drug particles adhering to its surface. These basic bodies are usually of different sizes. On account of the powder-laden suction air flowing through the annular chamber, the particles of powder are rendered more or less the same size, i.e. relatively large particles of powder are broken up as a result of the vortexing and the associated centrifugal forces. The powder-laden suction air is extracted by suction through the intermediate spaces which are formed between the wings extending radially outward from the cover and from where the suction air passes, in slightly concentrated form, into the mouthpiece of the metering device. It is possible to distribute, over the circumference of the cover, wings and interspaces of the same width, as seen in the circumferential direction. However, it is also possible to provide wings and/or interspaces of different widths in the circumferential direction. This creates at the end of the annular chamber, as seen in the direction in which flow takes place around the annular chamber, forced guidance of the powder-laden airstream, through an interspace provided correspondingly on the cover, into the mouthpiece. In a development of the subject matter of the invention, it is provided that some of the wings are of circumferentially wider configuration, in order to form a deflecting-wall wing for the powder-laden suction airstream. This wing is preferably directed, in first instance, in the axial direction of the annular chamber. The deflecting-wall wing forces the incoming suction airstream to deflect into a plane of circulation directed transversely to the annular chamber. By virtue of the deflecting-wall wing being acted upon at relatively high speed, relatively large particles of powder are broken up. The metering rod is retained in an inner cylinder, which can be rotated by the closure cap, such that it can be displaced along the axial extent of the inner cylinder. The rotation of the inner cylinder is transmitted to the metering rod. This inner cylinder is provided, on the lateral-wall side, with an axially running channel which extends from the emptying side of the metering chamber and terminates in the annular chamber, the deflecting-wall wing being provided in order to deflect the axial airstream direction into the orbital plane. Accordingly, this deflecting-wall wing is disposed in the manner of a cover in axial extension of the channel, with the radial outlet being left in the process. Via this channel, following the suction-air-induced raising operation of the piston and the associated release of the metering chamber, the separated-off dose of substance is sucked out and fed, via the annular chamber, to the user who is building up the suction airstream. In a preferred configuration, deflection from the radial flow direction into the axial flow direction is achieved by two channel deflection regions which are located directly one after the other and each cause flow to be deflected by 45 degrees. An intermediate channel portion which runs at an angle of approximately 45 degrees to a plane oriented transversely to the axis of the device, and connects the emptying side of the metering chamber to the axially running channel, is thus also preferably provided.

A total of two air-flow paths are created, of which the one causes the metering chamber to be emptied and the second leads directly into an annular chamber which is located upstream of the mouthpiece and where the two airstreams meet. Accordingly, the one particle-laden airstream established during the inhalation operation is channeled separately. The quantity of air which is required for inhalation is fed, in part, via the first air-flow path within the annular chamber. If the metering chamber is closed, the metering chamber can be opened via this air-flow path, for example via the suction-air-activated piston. By virtue of the air-flow paths being separated, a stream of air which is not laden with particles is formed initially. In the event of correct inhalation, approximately 50 liters of air per minute flow through the device, which quantities of air result from at least the two airstreams being added together, one fraction being fed, in first instance, via the first flow path, which opens the metering chamber. In a preferred configuration, this opening of the metering chamber, for example by virtue of a piston being displaced out of an emptying-standby position into an emptying-release position, takes place at an opening pressure of approximately 2 kPa, and furthermore with an airflow of 18 to 22 liters of air per minute. The airstream of the second air-flow path, which leads directly from the metering chamber into the annular chamber, the annular chamber being located upstream of the mouthpiece, has a significantly higher flow speed than the airstream which results in the metering chamber being emptied.

In a preferred configuration, the second airstream is sucked in through a grille-wall portion. The latter leaves a free opening cross-section which allows the necessary quantity of air to be easily sucked in. Further preferably, the air-inlet grille surface is located on the outer cylinder, which cannot be rotated in relation to the inner cylinder and continues the closure cap, on that side of the metering rod which is located opposite to the emptying direction of the metering chamber. This means that there is clear structural separation of the air-flow paths.

A compact construction of such a metering device is further achieved in that a flow channel directed toward the metering chamber is disposed beneath the air-inlet grille surface, even in the position assumed by the metering chamber in an emptying-standby position, and this flow channel even allows a visual check as to whether the metering chamber is full and/or closed. In a preferred configuration, this channel passes through the outer cylinder beneath the air-inlet grille surface for the first air-flow path in the region of an appropriately formed air-inlet opening. As a result of this configuration, the two air-flow paths open, in respect of the air-inlet openings, to the same side of the outer cylinder. Via the flow channel provided beneath the air-inlet grille surface, in the emptying-release position, the metering chamber is cleared preferably transversely to the device axis in order for the separated-off substance to be transported via the second air-flow path, passing through the annular chamber into the mouthpiece, all this being as a consequence of suction-air activation on the part of the user. In a further-preferred configuration, the interior of the inner cylinder is available entirely for the free distribution of the air sucked in through the air-inlet grille surface, and it is in flow connection with the annular chamber.

In a further configuration of the invention, the lateral wall of the outer cylinder has at least one air-inlet opening, preferably two radially opposite air-inlet openings. Further air-flow paths are achieved via these separate air-inlet openings, these further air-flow paths being separated from the other two air-flow paths at least in the emptying-standby position. It is thus provided, in an advantageous development of the subject matter of the invention, that the air-inlet openings open out in a tangentially directed manner into the annular chamber, a common flow direction being predetermined in the process, this further being a flow direction which is even predetermined by the other two air-flow paths. These air-inlet openings achieve a kind of initial ignition in order to deflect the rest of the air-flow paths in the desired flow direction within the annular chamber.

The substance which is to be inhaled is stored in a storage chamber, into which the metering chamber penetrates for filling purposes. In order to assist the filling operation of the metering chamber here, and furthermore to achieve the situation where the uppermost layer of the substance store, which has the metering chamber passing through it, is always loosened, a rotor-like blade is retained on the lower periphery of the inner cylinder, for example clipped thereon, which blade interacts with an inwardly directed stator-like shoulder of the storage-chamber wall. This allows the replenishment and the density of the substance in the storage chamber to be kept constant. Added to this is a loosening effect which is provided in the area surrounding the metering chamber and prevents fractions of the substance from coming to a halt. Furthermore, the rotor, in interaction with the stator, is configured such that, when the rotor-like blades are moved back when the closure cap is replaced and screwed on and the metering chamber is lowered into the storage chamber, the uppermost substance layer is subjected to slight contact pressure, in order thus to provide, in the storage chamber, an evened-out uppermost substance-quantity region associated with the metering chamber.

Finally, it has also proven to be advantageous to provide, in the region of the storage-chamber wall, a filling-level indicator which makes it possible to ascertain the amount of filling. In the simplest configuration, this can be coupled directly to the axial movement of a pressure piston which is disposed in the storage chamber and subjects the stored quantity of substance to loading from beneath in the direction of the inner cylinder. This pressure piston advances as substance is removed, and this can be observed via the filling-level indicator.

The invention is explained in more detail hereinbelow with reference to the accompanying drawing, which merely constitutes an exemplary embodiment and in which.

Figure 1:
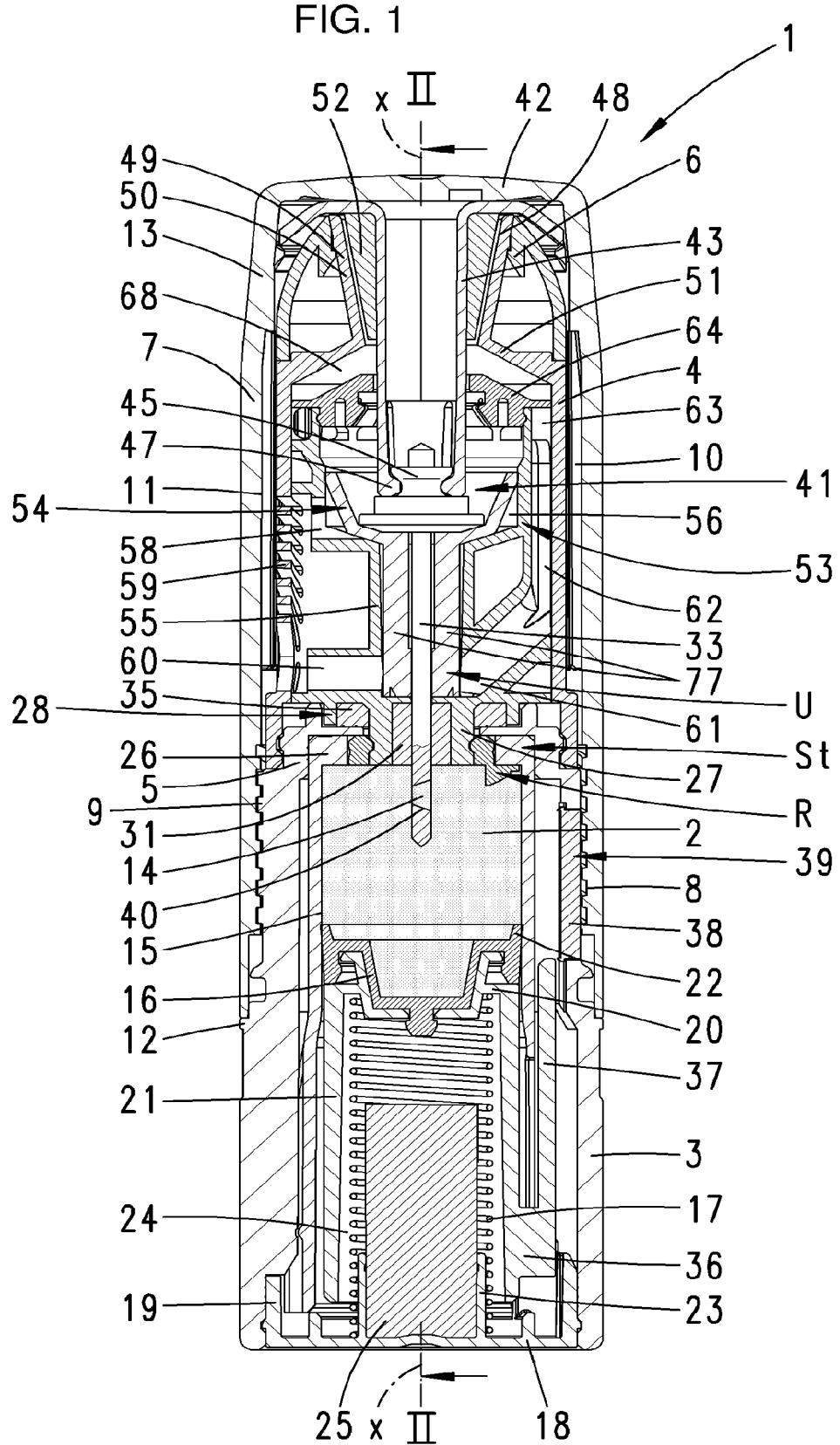
FIG. 1 shows the vertical section through a metering device according to the invention in the basic position, with the cap closed.
Figure 2:
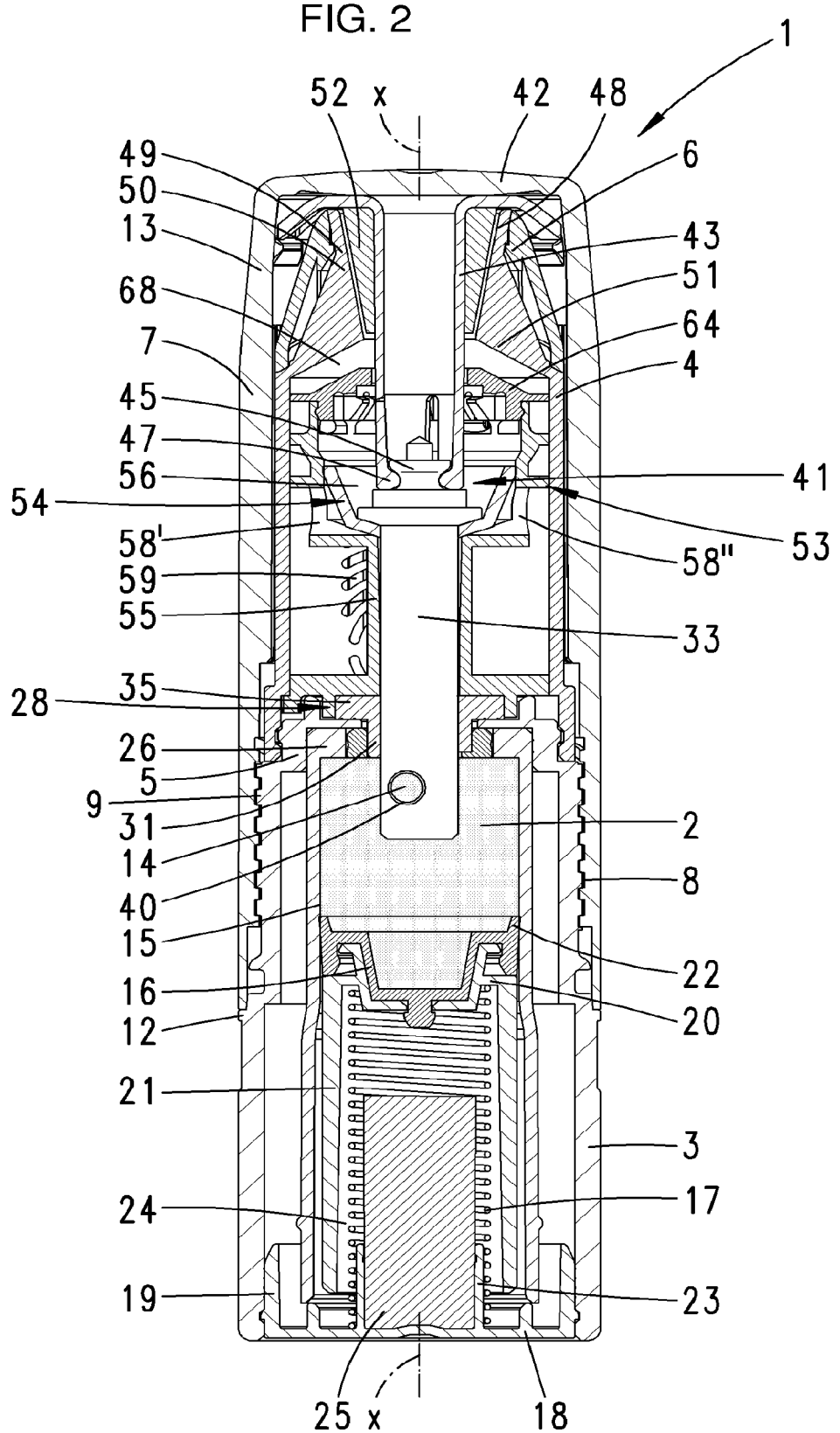
FIG. 2 shows a further vertical section along line II-II in FIG. 1.
Figure 3:
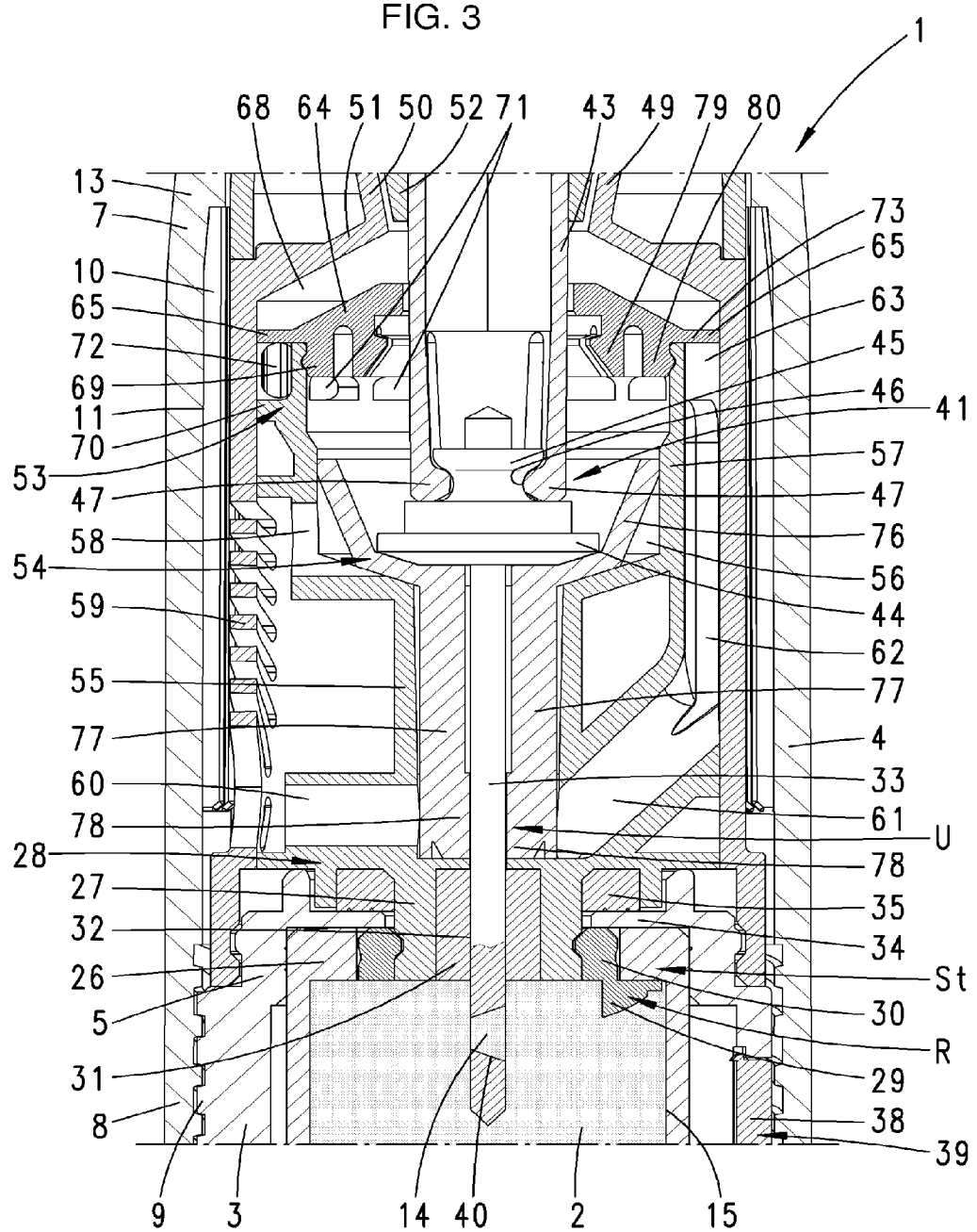
FIG. 3 shows an enlargement of an upper region of the device according to FIG. 1.

The metering device 1 which is illustrated in the figures and is intended for the inhalation of a pulverulent substance 2, in particular a medicinal substance, is realized as a short-elongate device which can readily be carried in a pocket and has a cylindrical housing 3 which determines its shape.

The cylindrical, tube-like housing 3 has, at the head end, an outer cylinder 4 which can be rotated about the device axis x relative to the housing 3. This outer cylinder is secured in a rotatable manner on the housing 3 in the region of an end-side radial step 5.

This likewise cylindrical, tube-like outer cylinder 4 merges, at the head end of the device 1, into an attached mouthpiece 6 which is formed appropriately for the mouth, for example is flattened. This mouthpiece 6 can have a cup-like closure cap 7 engaging over it in a protective manner. This closure cap is realized as a screw cap, for which reason an associated internal thread 8 engages in a corresponding external thread 9 on the lateral wall of the housing 3.

The outer cylinder 4 is connected to the closure cap 7 in a rotationally fixed manner, for which reason the outer cylinder has, on the outside of its lateral wall, vertically oriented ribs 10 which interact with correspondingly positioned, slot-like vertical grooves 11 on the inside of the wall of the closure cap 7. Accordingly, screw-action actuation of the closure cap 7 causes the outer cylinder 4 to be rotated about the device axis x.

At the foot end, the end periphery of the cup-like closure cap 7 engages in a stop-limiting manner, and with sealing via a cone, against an annular shoulder 12, which is achieved on account of the abovementioned step of the cylindrical housing 3.

The closure cap 7 serves, at the same time, as an actuating handle 13 for dispensing the pulverulent substance 2 in reproducible sub-quantities 14, for which purpose use is made of the axial screw-action displacement provided by the threaded engagement between the internal thread 8 and external thread 9. The substance 2 is accommodated (possibly such that it can be refilled) in a storage chamber 15 of the housing 3. A metering device conveys a respective sub-quantity 14 of substance to a transfer location U located outside the storage chamber 15.

The meterable substance is a (usually medicinal) pulverulent substance 2. It is possible for basic bodies such as lactose, which are capable for example of transporting a suction stream, to be carriers for fine micronized drug particles adhering to the surface.

The storage chamber 15 is terminated at the bottom by a cup-like pressure-exerting base 16, which is spring-loaded in the direction of the mouthpiece 6 by means of a compression spring 17. The compression spring 17 has its foot-side end turn supported on a base cap 18, which closes the housing 3 there. This base cap is in latching engagement with that portion of the housing 3 which is of larger cross-section here on its inside wall, a corresponding latching collar 19 of the base cap 18 engaging in a matching annular groove of the housing 3.

The head-side end turn of the biased compression spring 14 subjects an inner shoulder 20 of a hollow piston 21 of the piston-like means 16/21 to loading action. As can be seen from the illustrations, the pressure-exerting base 16, which is in the form of a graduated cup, is connected with latching action to the hollow piston 21 in the region of the inner shoulder 20.

The cup periphery of the pressure-exerting base 16 forms an annular lip 22 which, on account of its elastomeric material, strips substance off the wall of the storage chamber 15 without leaving any residues.

Figure 4:
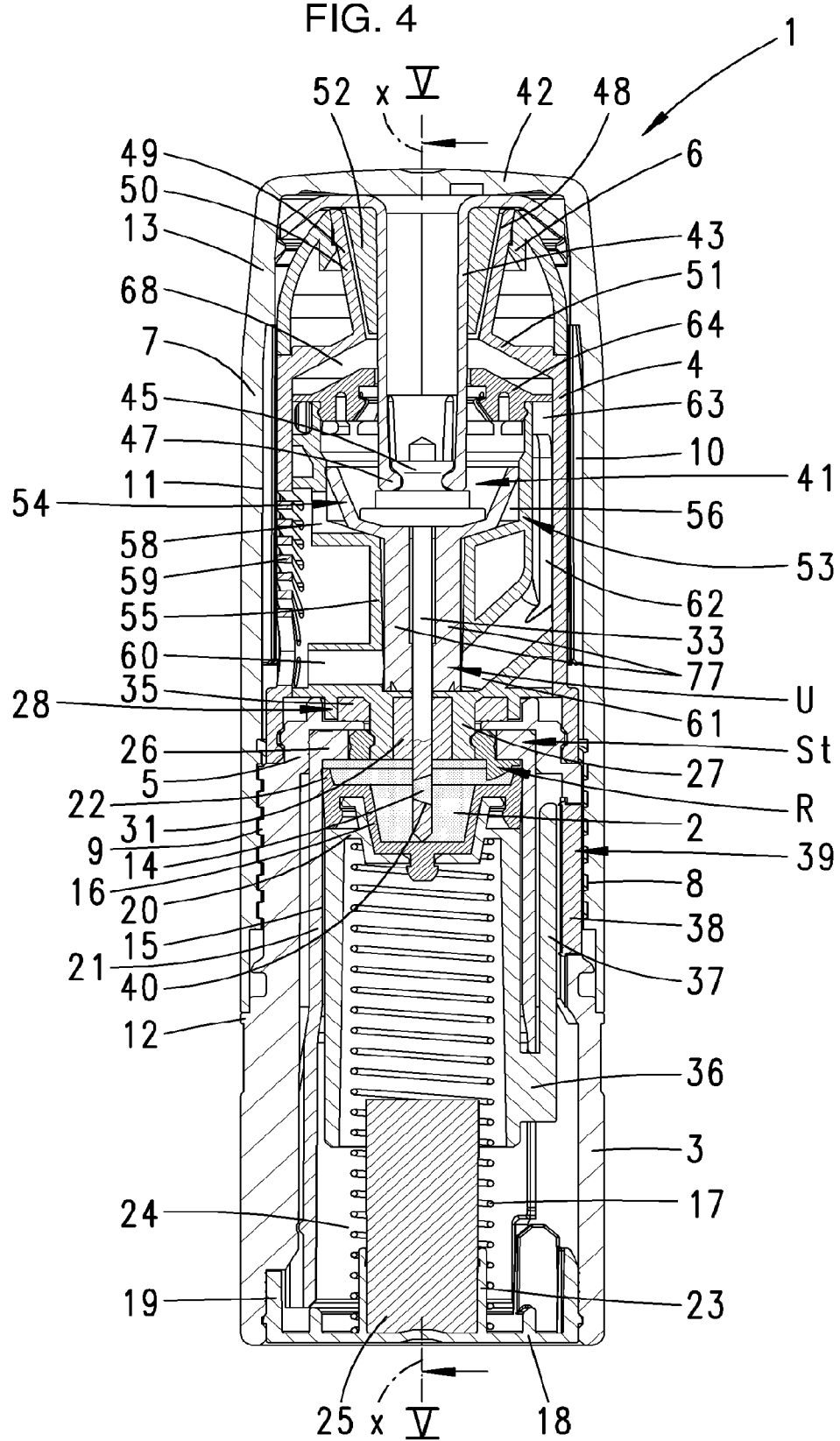
FIG. 4 shows a sectional illustration corresponding to FIG. 1, relating to the situation where the storage chamber for the substance which is to be inhaled has been more or less emptied.
Figure 5:
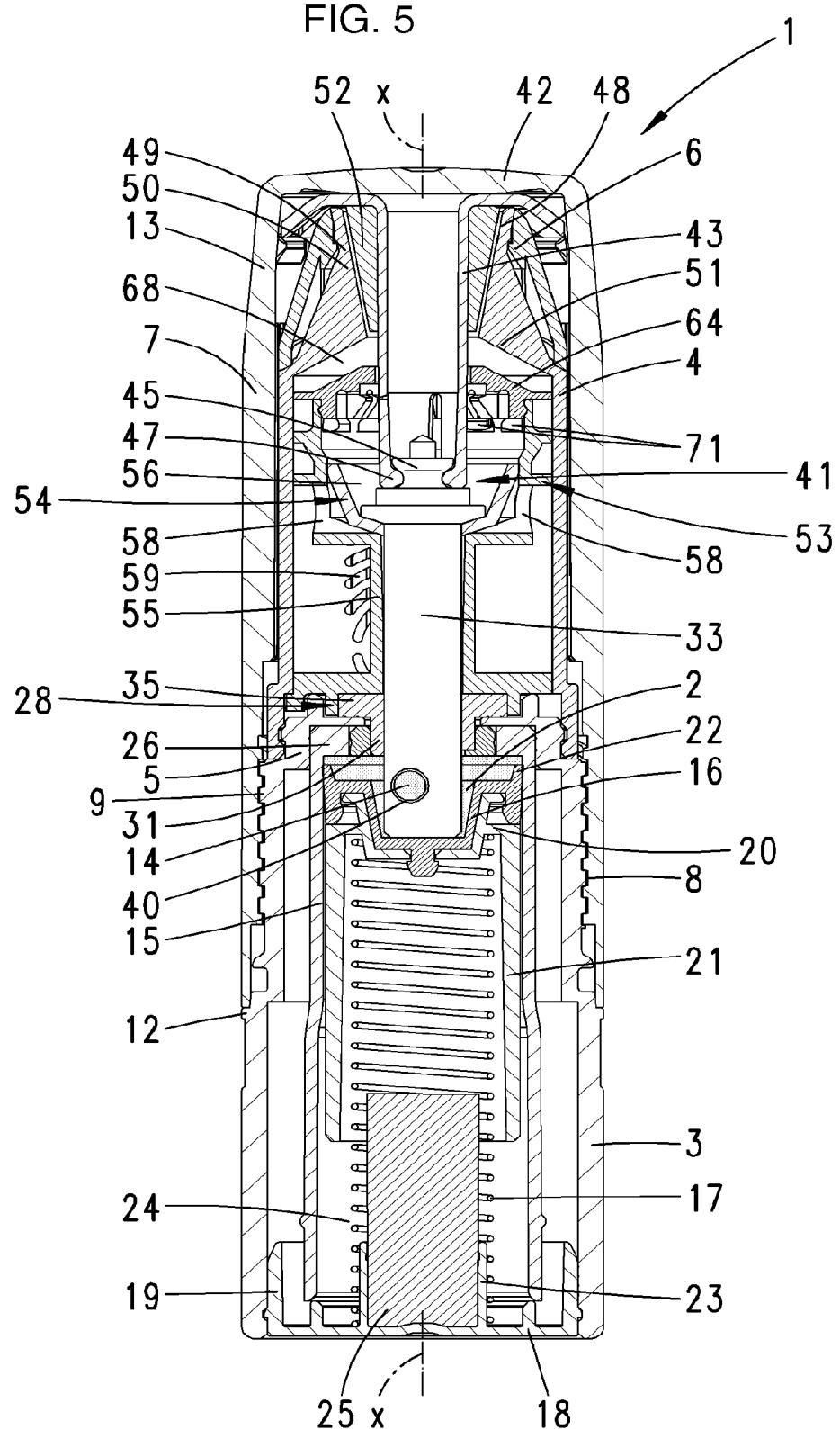
FIG. 5 shows the section along line V-V in FIG. 4.

In the exemplary embodiment illustrated, the compression spring 17 is a cylindrical spring which, in the state in which it is relieved of stressing, has a length corresponding approximately to ten times the maximum contact-pressure length. The contact-pressure length is defined by the extent of axial displacement of the pressure-exerting base 16 between a lower position according to FIG. 1, this position corresponding to the filling position, and an upper, stop-limited position of the pressure-exerting base 16 in the storage chamber 15 according to FIG. 4. Thus, the exemplary embodiment illustrated provides a contact-pressure length of 15 mm. As a result of the configuration of the spring, in particular as a result of the selected length of the spring, the pressure-exerting base 16 is subjected to a constant spring pressure over the entire contact-pressure length, and this leads to the substance being compressed uniformly throughout the duration of use of the device 1.

A hollow upright stub 23 extends centrally from the base cap 18. Together with the hollow piston 21 which encloses it at a distance apart, this hollow upright stub forms a chamber 24 for the compression spring 17. The hollow upright stub 23 contains, in its center, a moisture-absorbing material in the form of a drying-agent capsule 25. At the transition to the outer cylinder 4, which follows the housing 3 in the axial direction, the storage chamber 15 terminates with a chamber ceiling 26 formed integrally with the lateral wall of the storage chamber 15. Passing through the center of this chamber ceiling is a cylinder portion 27 of a rotary part 28 which extends in a plane perpendicular to the device axis x. This rotary part is of substantially plate-like configuration and is connected in a rotationally fixed manner to the outer cylinder 4 and, accordingly, can be rotated about the device axis x in relation to the chamber ceiling 26. The cylinder portion 27 extends on the underside of the rotary part 28, passing through the chamber ceiling 26. The lower free end surface of the cylinder portion 27 is located in the plane of that surface of the chamber ceiling 26 which covers the storage chamber 15.

The diameter of the through-opening in the chamber ceiling 26 is larger than the diameter of the cylinder portion 27. A holder, of annular shape in plan view, for a rotor blade R, is positioned in the annular gap which remains. This rotor blade is connected in a rotationally fixed manner to the cylinder portion 27.

The inner surface of the rotor ring 30, this inner surface being directed toward the storage chamber 15, is located in the plane of the correspondingly directed end surface of the cylinder portion 27.

Figure 22:
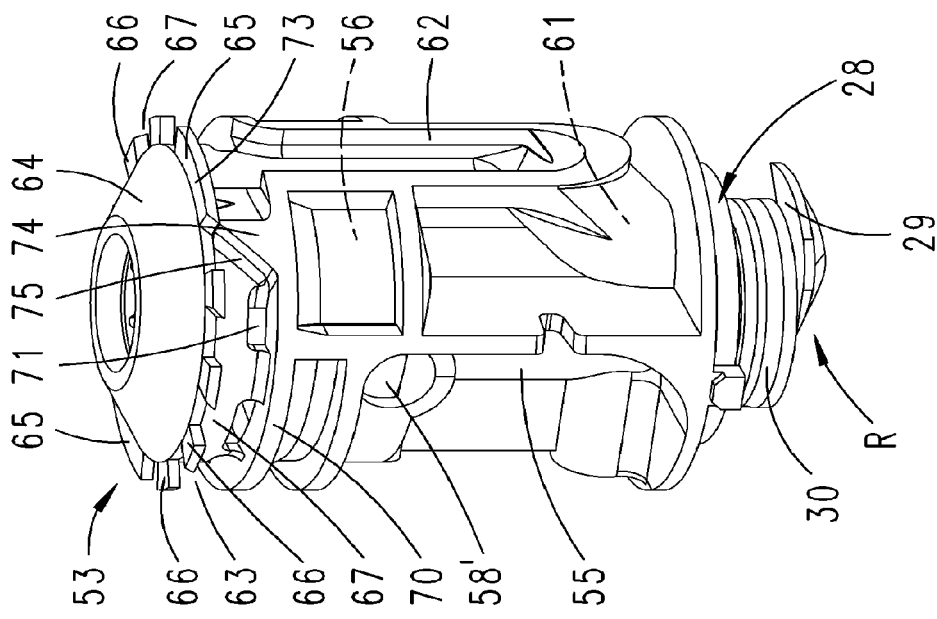
FIG. 22 shows a further perspective illustration of the inner cylinder.
Figure 23:
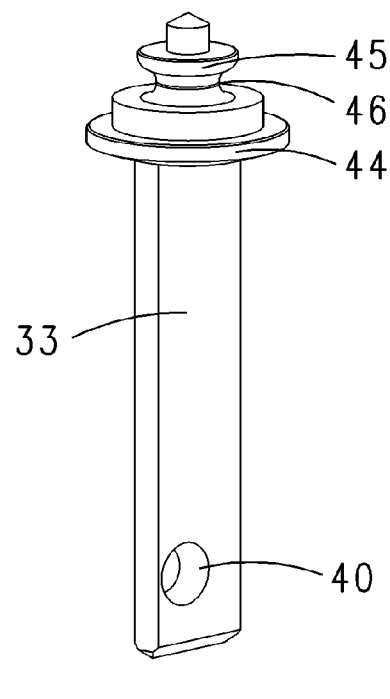
FIG. 23 shows a perspective detail illustration of the metering rod of the metering device.
Figure 24:
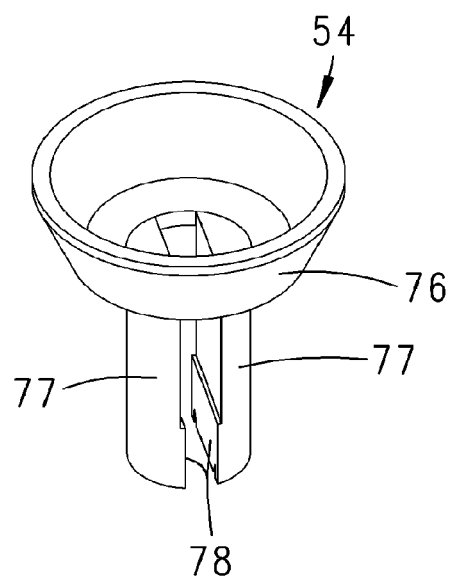
FIG. 24 shows a perspective detail illustration of the piston.
Figure 25:
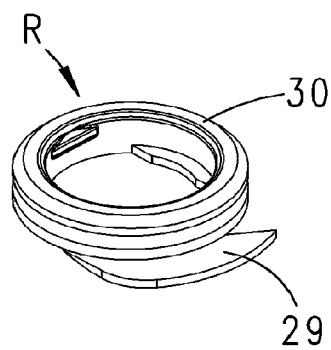
FIG. 25 shows a further perspective detail illustration of a rotor-like blade for disposing on the inner cylinder.
Figure 26:
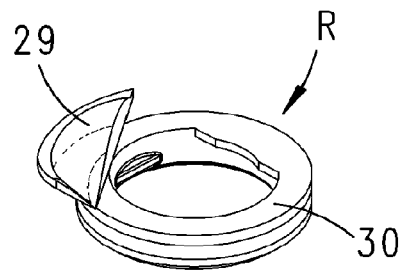
FIG. 26 shows a further perspective illustration of the rotor-like blade.

The rotor R, which is illustrated on its own in FIGS. 22 and 23, carries on the underside, that is to say in the direction toward the storage chamber 15, a blade 29. This is a blade 29 which is in the form of a spherical-cap portion and projects radially outward beyond the ring 30 of the rotor R. The blade 29 correspondingly engages beneath that region of the chamber ceiling 26 which adjoins the rotor R radially on the outside, that surface of the blade 29 which is directed toward the chamber ceiling 26 being of planar configuration. This surface of the blade 29 engages against the top surface of the chamber which is directed toward the blade. The blade 29 extends radially as far as the inner wall of the storage chamber 15. From this radially outer region, the blade 29 slopes up convexly in the radially inward direction, as seen in cross-section, to an axial height corresponding approximately to the extent by which the blade 29 projects radially beyond the rotor ring 30.

As a result of this arrangement, the blade 29 of the rotor R projects into the substance stored in the storage chamber 15. The shoulder formed by the chamber ceiling 26, in interaction with the blade 29 or rotor R, which can be rotated relative to the storage chamber 15, forms a stator St.

The rotor R is clipped on the cylinder portion 27 of the rotary part 28 via the rotor ring 30.

The cylinder portion 27 accommodates a sealing bushing 31 in its center. This bushing consists of a rubber material or a similar elastic material. This leaves, in its center, a cross-sectionally slot-like guide opening 32 for a cross-sectionally adapted metering rod 33.

In the simplest configuration, the sealing bushing 31 and also an annular seal 35 provided between the rotary part 28 and a housing portion 34, which engages over the chamber ceiling 26 on the housing side, may be produced by two-component injection molding together with the rotary part 28 and, furthermore, with an inner cylinder, which will be described in more detail. It is also possible in this respect, however, for the rubber or elastomer parts to be provided subsequently during production.

At the foot end, the hollow piston 21, which is connected with latching action to the pressure-exerting base 16, has a radial extension arm 36. Integrally formed on the latter is an axially oriented indicating protrusion 37 which engages over the storage-chamber wall on its outside. The axial position of this indicating protrusion, this position being reached in dependence on the position of the pressure-exerting base, can be seen by the user from the outside through a viewing window 38 provided in the housing. A filling-level indicator 39 is provided as a result.

The metering rod 33 is appropriately configured for functioning as a moving metering chamber 40 for the sub-quantity 14 of substance which is to be dispensed, the metering rod 33 moving linearly along the longitudinal center axis x-x of the substantially rotationally symmetrical device 1, and this being accompanied by a rotary movement executed about the longitudinal center axis x-x. The metering rod 33 is formed substantially as a flat part with an elongate-rectangular cross-section. The length ratio of narrow side to broad side is approximately 1:3 in the exemplary embodiment illustrated.

Figure 20:
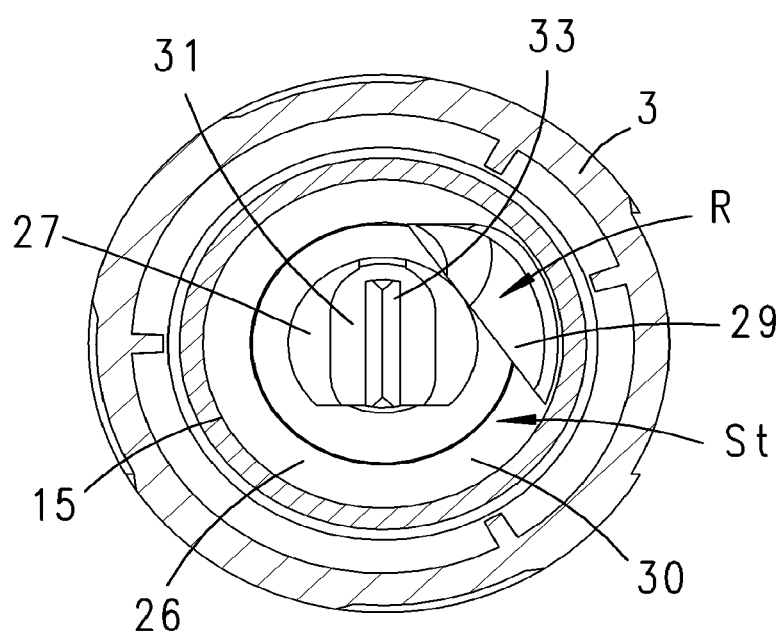
FIG. 20 shows the section along line XX-XX in FIG. 11 through the storage chamber, with the substance which is stored here having been left out.
Figure 21:
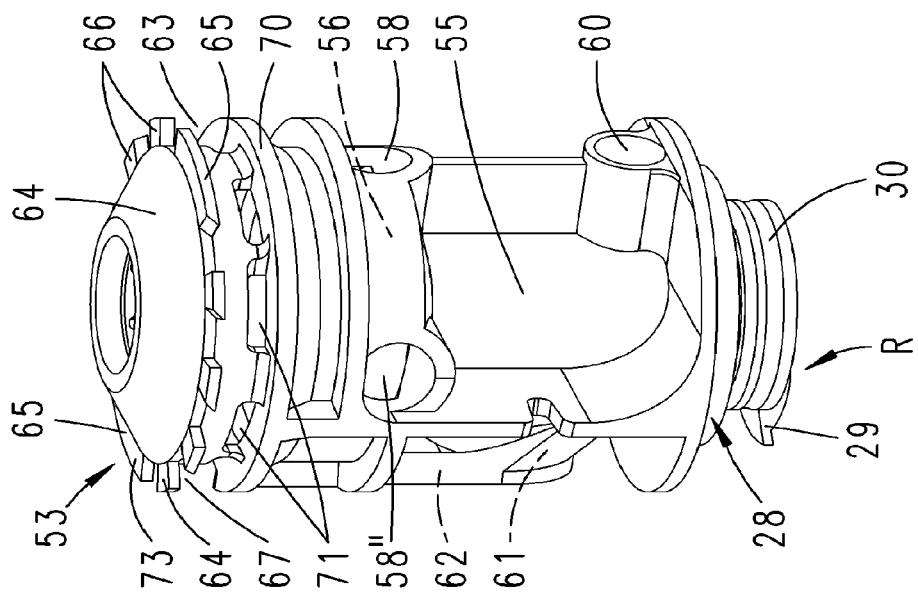
FIG. 21 shows a perspective detail illustration of an inner cylinder of the metering device.

At the end which is directed away from the mouthpiece 6, the metering rod 33 forms a portion which tapers to a point more or less in the manner of a cross-recessed screwdriver tip. The two mirror-symmetrical oblique flanks here extend from the respective broad sides of the metering rod 33 (cf. FIG. 20).

On account of the metering rod 33 being carried along in rotation, the cross-sectional configuration of the metering rod 33 and the tapering of the free end region have a loosening, displacing effect in the central region in relation to the mass of pulverulent substance 2.

The metering chamber 40 is realized as a transverse hole which runs substantially perpendicularly to the longitudinal center axis x-x and has an axis which passes through the broad-side surfaces of the metering rod 33. The transverse hole is formed conically, so that the transverse hole tapers in the direction of one broad-side surface of the metering rod 33. Furthermore, as can be seen for example from the illustration in FIG. 2, the metering chamber 40, which is formed in the region of that end of the metering rod 33 which projects into the mass of substance, is disposed eccentrically in relation to the broad-side surfaces of the metering rod 33, that is to say it is offset laterally in relation to the longitudinal axis x-x.

The displacement path of the metering chamber 40, which moves linearly, and, at the same time, in rotation, allows, in both end positions of the metering rod 33, for the cross-section of the guide opening 32 to be kept closed, with metering-chamber-filling scraping or stripping action over the length of the said opening 33.

The mouthpiece end of the closure cap 7 forms a docking location 41 between the metering rod 33 and closure cap 7, this docking location disengaging when subjected to overloading. The latching means on the closure-cap side here is a resilient hook annulus which is formed in the region of the free end of a hollow cylinder 43 disposed centrally on the underside of a closure-cap ceiling 42. The corresponding end of the metering rod 33 is rotationally symmetrical in cross-section, a disk-like radial collar 44, furthermore, projecting out in the transition region from the flat-part portion to the cylindrical end portion. At an axial spacing from this radial collar 44, that end region of the metering rod 33 which is directed away from the flat part forms a latching head 45. A wasp-waist-like annular groove 46 is formed between this latching head and the radial collar 44. Inwardly directed noses 47 of the resilient tongues of the hook annulus engage in this annular groove. The noses 47 can pass over the latching head 45 in both axial directions. The latching action may be fairly tight, since it is released and reinstated during the screwing-action displacement of the cap.

The central opening 48 of the mouthpiece 6 is formed in the region of a dispersing part 49. This dispersing part 49 opens conically outward, that is to say in the direction away from the storage chamber 15, the wall 50 of the dispersing part merging, in the direction toward the storage chamber 15, into an annular, roof-like ceiling portion 51. At the same time, the latter forms the upper terminal of the outer cylinder 4, which carries the mouthpiece 6.

The central free space created by the dispersing part 49 has the hollow cylinder 43, which carries the noses 47, passing through it centrally in the cap-closed position. The annular space which forms here between the hollow cylinder 43 and the dispersing-part wall is filled by a further drying-agent capsule 52 in the cap-closed position.

The outer cylinder 4 accommodates an inner cylinder 53, passing through the center of which is the metering rod 33 and, in the cap-closed position, the hollow cylinder 43 belonging to the closure cap. The inner cylinder is connected in a rotationally fixed manner to the outer cylinder 4.

This inner cylinder 53 is configured substantially as a hollow body and carries, in its center, an axially displaceable piston 54. The piston 54 is guided more or less in the lower half of the inner cylinder 53, directed toward the storage chamber 15, by a cross-sectionally round guide portion 55.

That portion of the inner cylinder 53 which is directed away from the storage chamber 15 forms a piston-head displacement region 56 which has a cross-section larger than that of the guide portion 55 and of which the axially oriented wall 57 has radial openings 58, 58' and 58". These radial openings are in flow connection with a grille-wall portion 59 of the outer cylinder.

Formed beneath the grille-wall portion 59, and furthermore at the foot end of the guide portion 55 of the inner cylinder, is a radially oriented flow channel 60, which likewise opens toward the grille-wall portion 59. This flow channel may also serve as a window for visually monitoring the metering rod 33. It opens out into the free space left in the center by the guide portion 55. Radially opposite the flow channel 60, the guide portion 55 is adjoined by an intermediate channel portion 61 which, starting from the guide portion 55, and with the inclusion of an angle of 45° in relation to a plane oriented perpendicularly to the axis x, slopes up in the direction of the associated wall of the outer cylinder 4 in order then to merge, at the end, into an axially directed channel 62. This channel 62 is formed by an axially oriented, slot-like, radially outwardly opening recess in the lateral surface of the inner cylinder. The channel 62 is covered over radially by the associated wall of the outer cylinder 4.

As well as the radial opening 58, which can be seen by way of example in the sectional illustration in FIG. 1, two further radial openings 58' and 58" are provided, and these each enclose, as seen in a plane oriented transversely to the axis x, an angle of 90° in relation to this radial opening 58 and, by virtue of the inner-cylinder wall being configured appropriately, are in direct air-flow connection with the grille-wall portion 59.

The axially oriented channel 62 has its end which is directed toward the mouthpiece 6 opening out into an annular chamber 63. The latter forms a vortex chamber. The ceiling 64 of the latter is of cross-sectionally roof-like configuration and is provided with peripherally extending, projecting wings 65, 66. These engage peripherally against the inner wall of the outer cylinder 4 and, as seen in the circumferential direction, leave intermediate spaces 67 between them, through which an air-flow connection is achieved between the annular chamber 63 and a further annular space 68 left between the dispersing-part ceiling portion 51 and the annular-chamber ceiling 64.

The ceiling 64 is secured on the inside wall of the inner cylinder 53 by an axially directed flange 69.

The base of the annular chamber 63 is formed by an annular collar 70 which projects radially outward on the outside wall of the inner cylinder 53 at an axial spacing from the wings 65, 66 of the ceiling 64. It is also the case that this annular collar is supported peripherally on the inside wall of the outer cylinder 4. This annular collar 70 is interrupted by the axially oriented channel 62. The annular chamber 63 is bounded in the radially inward direction by an end-side wall portion which belongs to the inner cylinder 53 and serves for latching the ceiling 64. The resulting annular-chamber wall is provided with slot-like through-passages 71 in order to provide air-flow connection between the annular chamber 63 and the piston-head displacement region 56.

Figure 18:
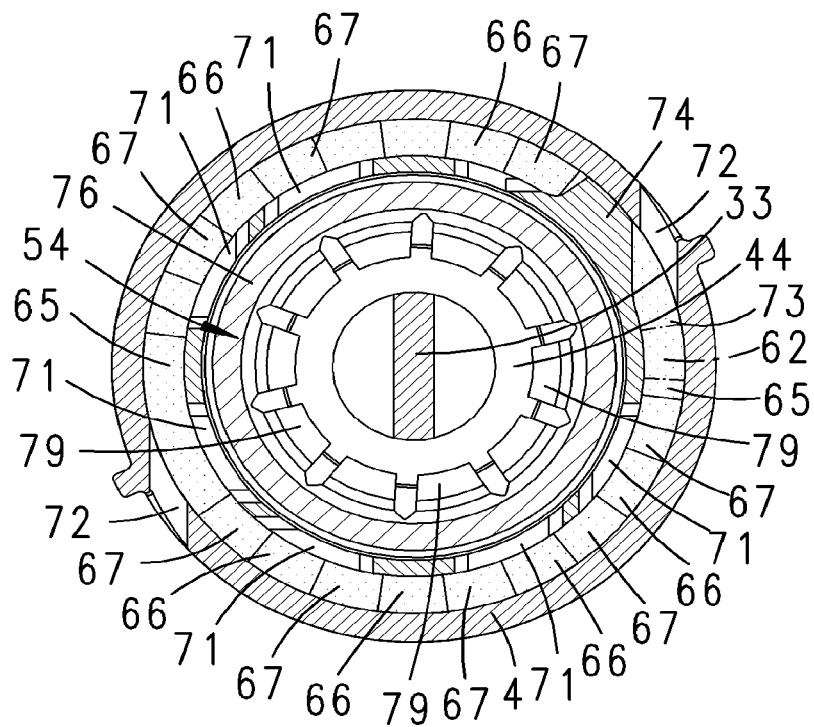
FIG. 18 shows the cross-sectional illustration through the metering device along line XVIII-XVIII in FIG. 11.
Figure 19:
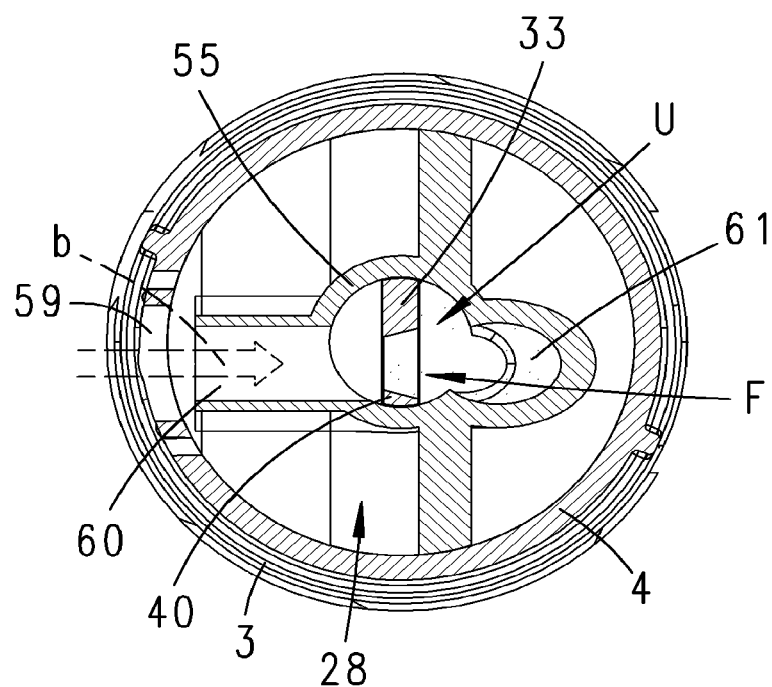
FIG. 19 shows an illustration which corresponds to FIG. 17 and has been taken along line XIX-XIX in FIG. 11, relating to the emptying-release position.

As can furthermore be seen, in particular, from the sectional illustration in FIG. 18, the outer-cylinder wall is provided, level with the annular chamber 63, with two diametrically opposite air-inlet openings 72. These open out tangentially into the annular chamber 63, and this, furthermore, predetermines a common flow direction. Accordingly, a sucking-in action through the air-inlet openings 72 results in a predetermined air flow in the annular chamber 63. The axially oriented channel 62 opens out, as seen in the flow direction, immediately downstream of the mouth of one air-inlet opening 72 in the annular chamber 63, so that the airstream entering into the annular chamber 63 through the axial channel 62 is deflected specifically in the desired vortexing direction via the air-inlet openings 72.

The wings of the ceiling 64 are of different widths as seen in the circumferential direction. Thus, two diametrically opposite wings 65 are approximately three times the width of the rest of the wings 66, as seen in the circumferential direction. One of these broader wings 65 covers over the mouth region of the axial channel 62 into the annular chamber 63 and, accordingly, forms a deflecting-wall wing 73 for the suction airstream entering into the annular chamber 63 through the axial channel 62.

Figure 27:
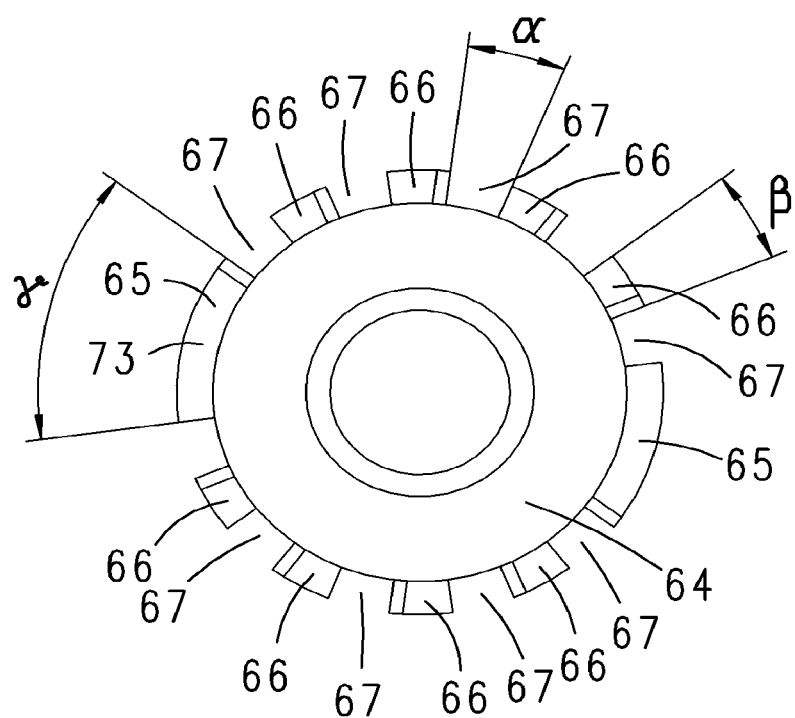
FIG. 27 shows, in a detail drawing, the bottom view of a cover of an annular chamber.

As can further be seen, in particular, from the illustration in FIG. 27, the wings 66 extend circumferentially, in the exemplary embodiment described, over an angle $\beta$ of 15°. The intermediate spaces 67 left between the wings 66 and 65 likewise extend circumferentially over an angle $\alpha$ of 15°, while the peripheral edges of the broader wings 65 enclose an angle $\delta$ of 45°.

Other distributions are also possible in this respect (for example smaller wings—larger intermediate spaces; larger wings—smaller intermediate spaces; irregular configuration of wings and intermediate spaces).

An interrupter 74 is disposed in the annular chamber 63 adjacent to the mouth of the axial channel 62 in the annular chamber 63, the interrupter being in the airflow direction through the air inlet openings 72. This interrupter limits the circumferential path of the annular chamber 63 and, accordingly as a result of this configuration, this path is of an interrupted form rather than being annular throughout. The rear flank of the interrupter 74, this flank being oriented counter to the flow direction, constitutes a run-on slope 75, connecting the annular-chamber base to the annular-chamber ceiling, which contains the intermediate spaces 67. This causes the airstream in the end region of the annular chamber 63 to be forcibly deflected axially upward into the further annular space 68.

The piston 54, which is retained in a rotationally fixed, but axially displaceable manner, in the inner cylinder 53, has, in first instance, a piston head 76 which opens in disk form in the direction of the mouthpiece. This piston head opens conically in cross-section. Two parallel, axially oriented tongues 77 are integrally formed on the underside of the piston disk. The piston 54 consist of a rubber-like material.

Along their lower free periphery, the tongues 77, which accommodate the cross-sectional contour of the guide portion 55 of the inner cylinder 53 on their outside wall, are split in a lip-like manner and, furthermore, in their free peripheral region, they have material-reinforced sealing surfaces 78.

The flat part of the metering rod 33 is guided between the tongues 77, the sealing surfaces 78, in interaction with the flat part of the metering rod 33, having a stripping and sealing action.

In a basic position of the device according to the illustration in FIG. 1, the free peripheries of the tongues 77, these peripheries being split in a lip-like manner, engage, within an axial depression, against the upper side of the cylinder portion 27.

Furthermore, in this basic position, the disk-like piston head 76 rests in a stop-limited manner on a base region of the piston-head displacement region 56. The encircling peripheral region of the free end of the piston head 76 engages with sealing action against the associated inner wall of the inner cylinder 53.

Furthermore, in this basic position, the head of the metering rod 33, that is to say the radial collar 44 and latching head 45 of the same, rests in the depression created by the disk-like configuration of the piston head 76.

The piston head 76 here is located at an axial distance beneath the ceiling 64.

Figure 6:
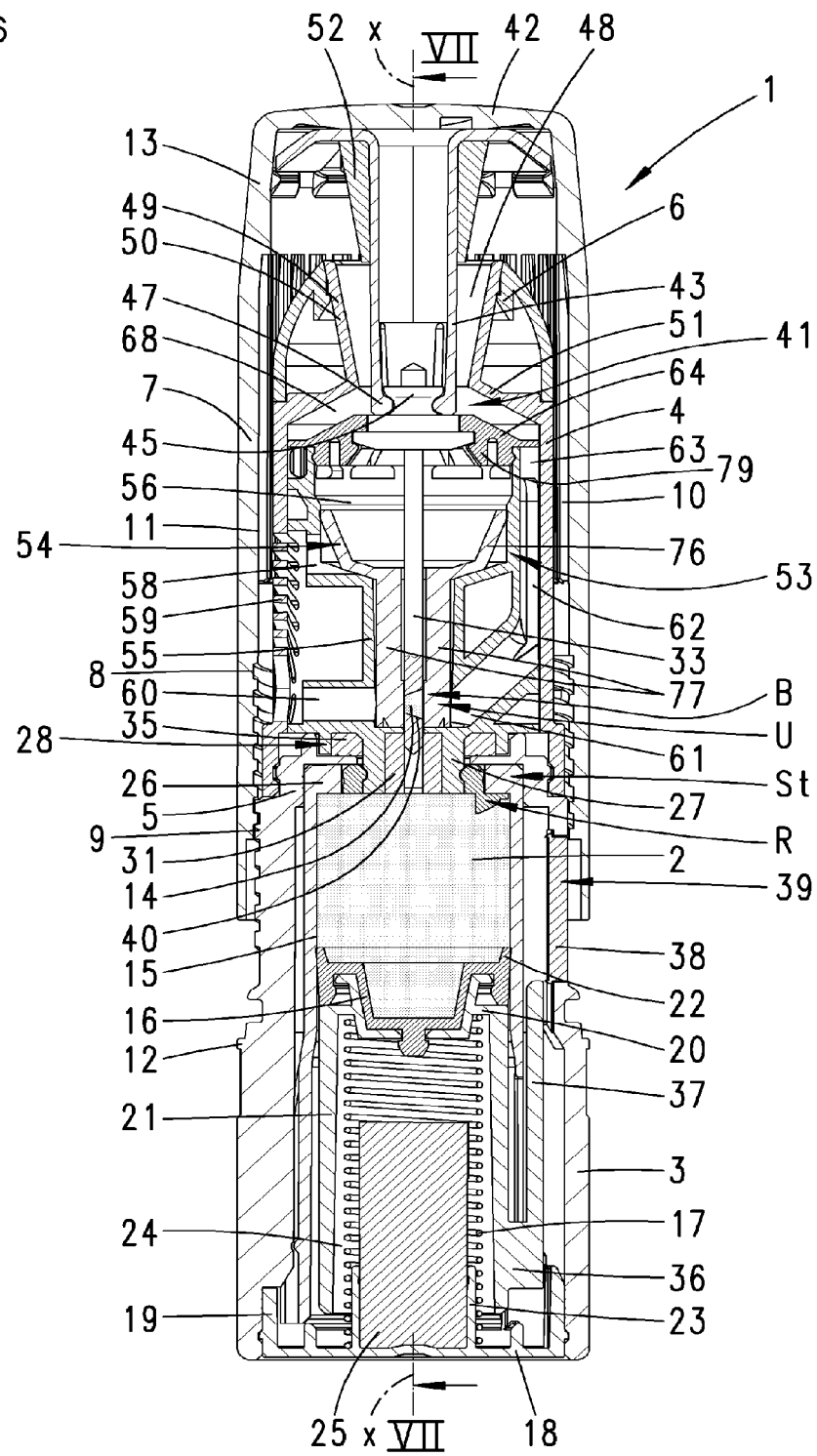
FIG. 6 shows a further illustration corresponding to FIG. 1, this time during removal of the closure cap.
Figure 7:
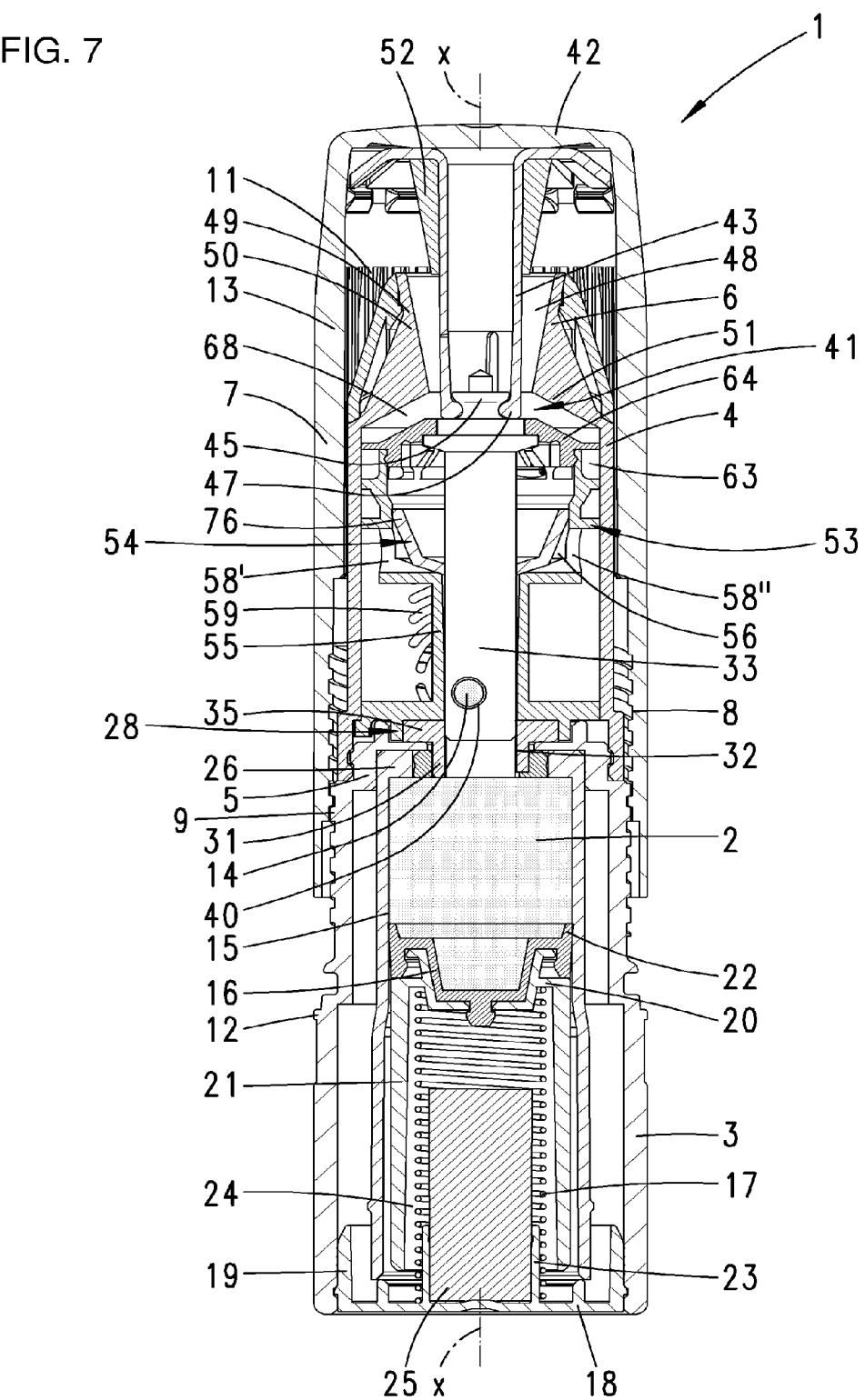
FIG. 7 shows the section along line VII-VII in FIG. 6.
Figure 8:
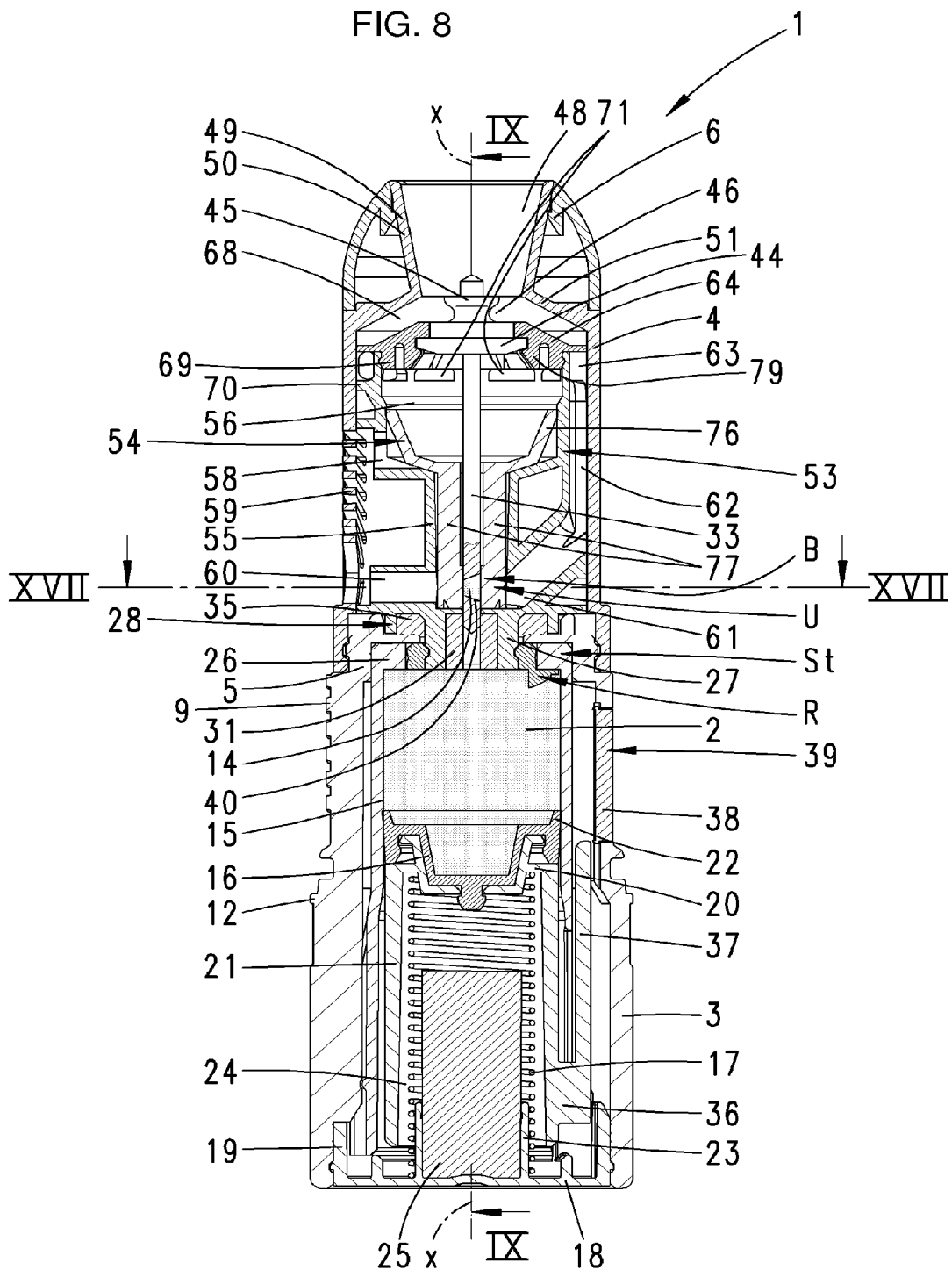
FIG. 8 shows the vertical section according to FIG. 1, but following removal of the closure cap and the resulting displacement of a metering chamber into the emptying-standby position.
Figure 9:
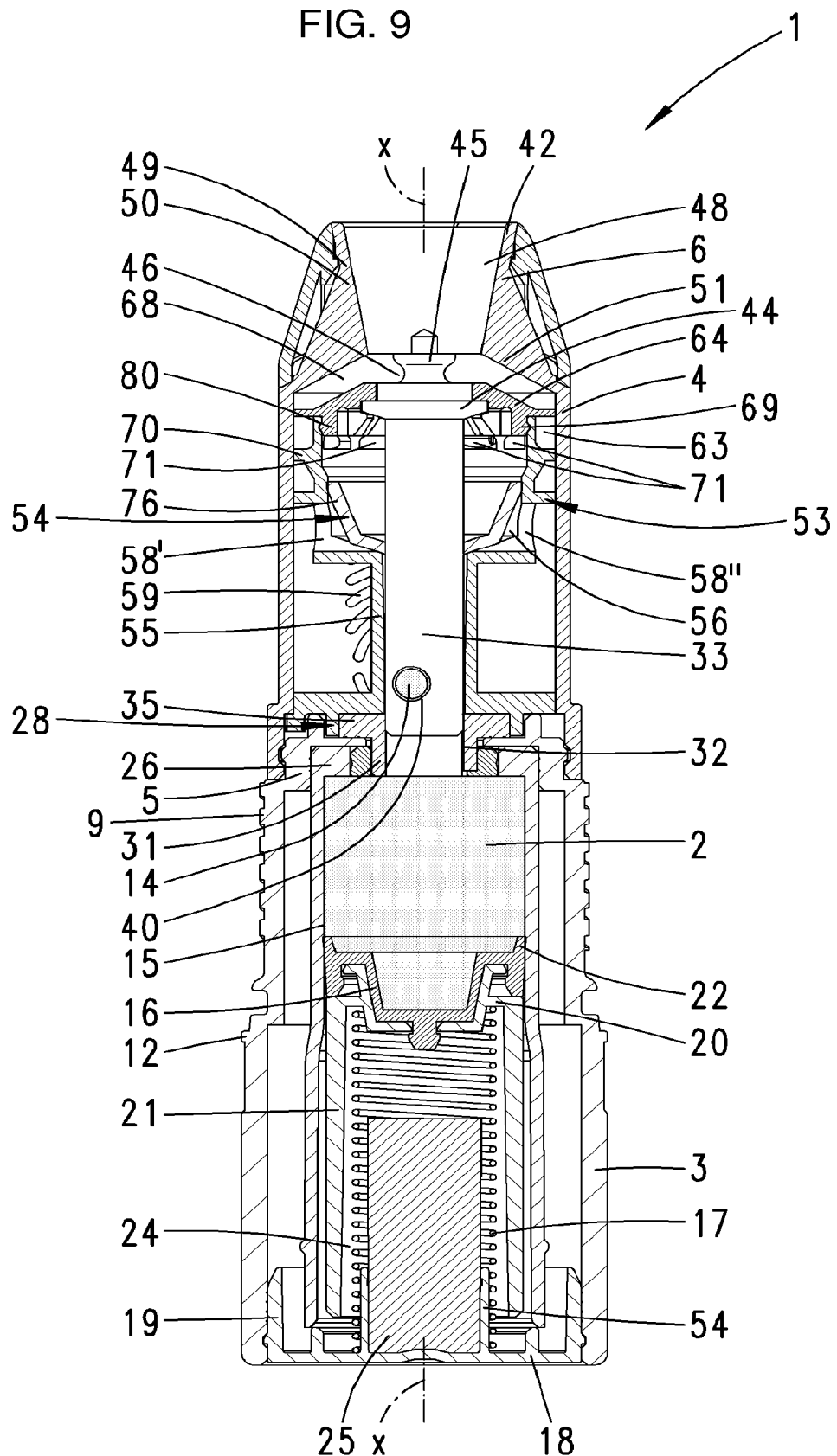
FIG. 9 shows the section along line IX-IX in FIG. 8.
Figure 10:
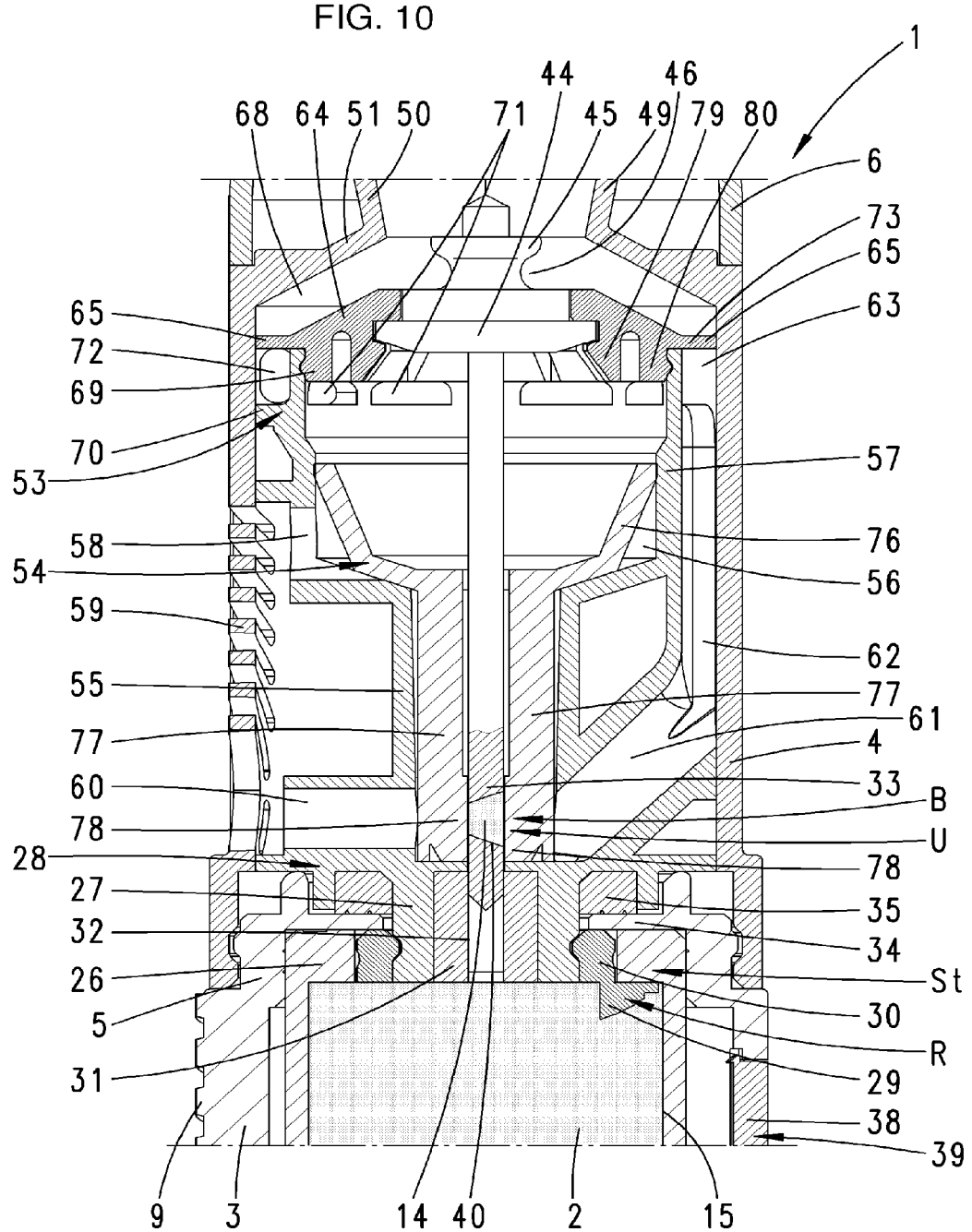
FIG. 10 shows a detail-view illustration corresponding to FIG. 3, relating to the situation according to FIG. 8.
Figure 11:
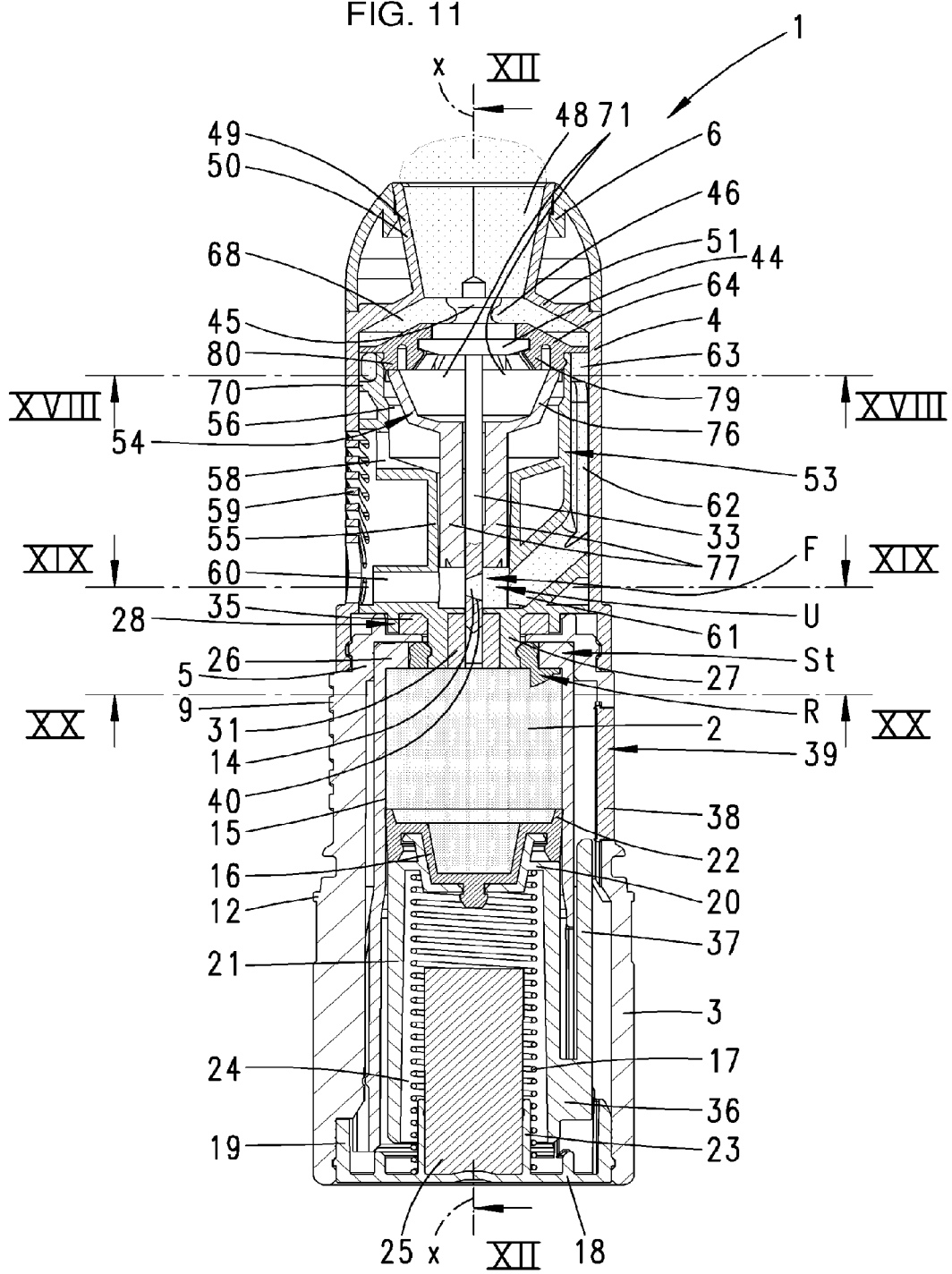
FIG. 11 shows a follow-up illustration to FIG. 8, but relating to a position assumed during inhalation.
Figure 12:
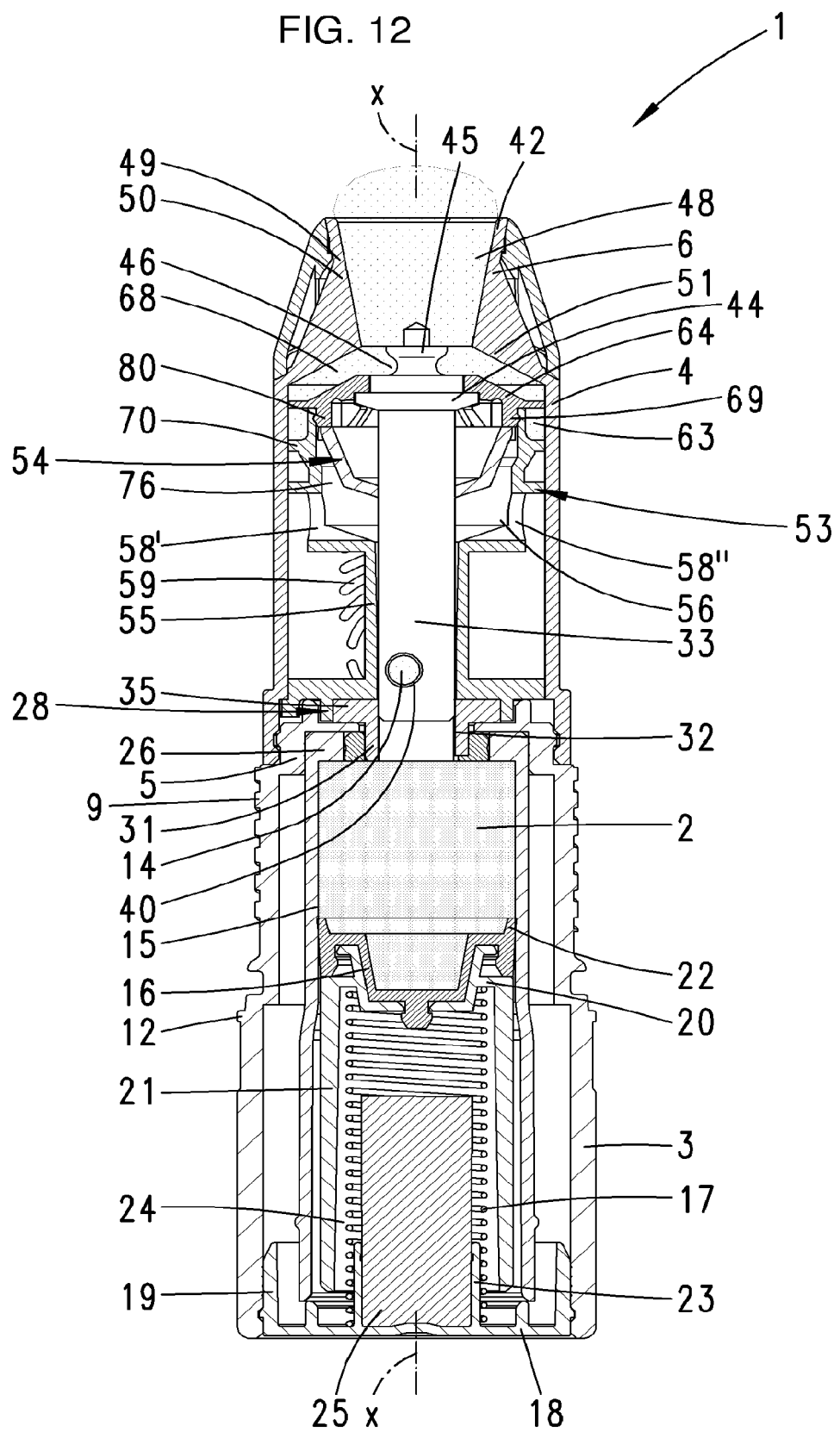
FIG. 12 shows the section along line XII-XII in FIG. 11.
Figure 13:
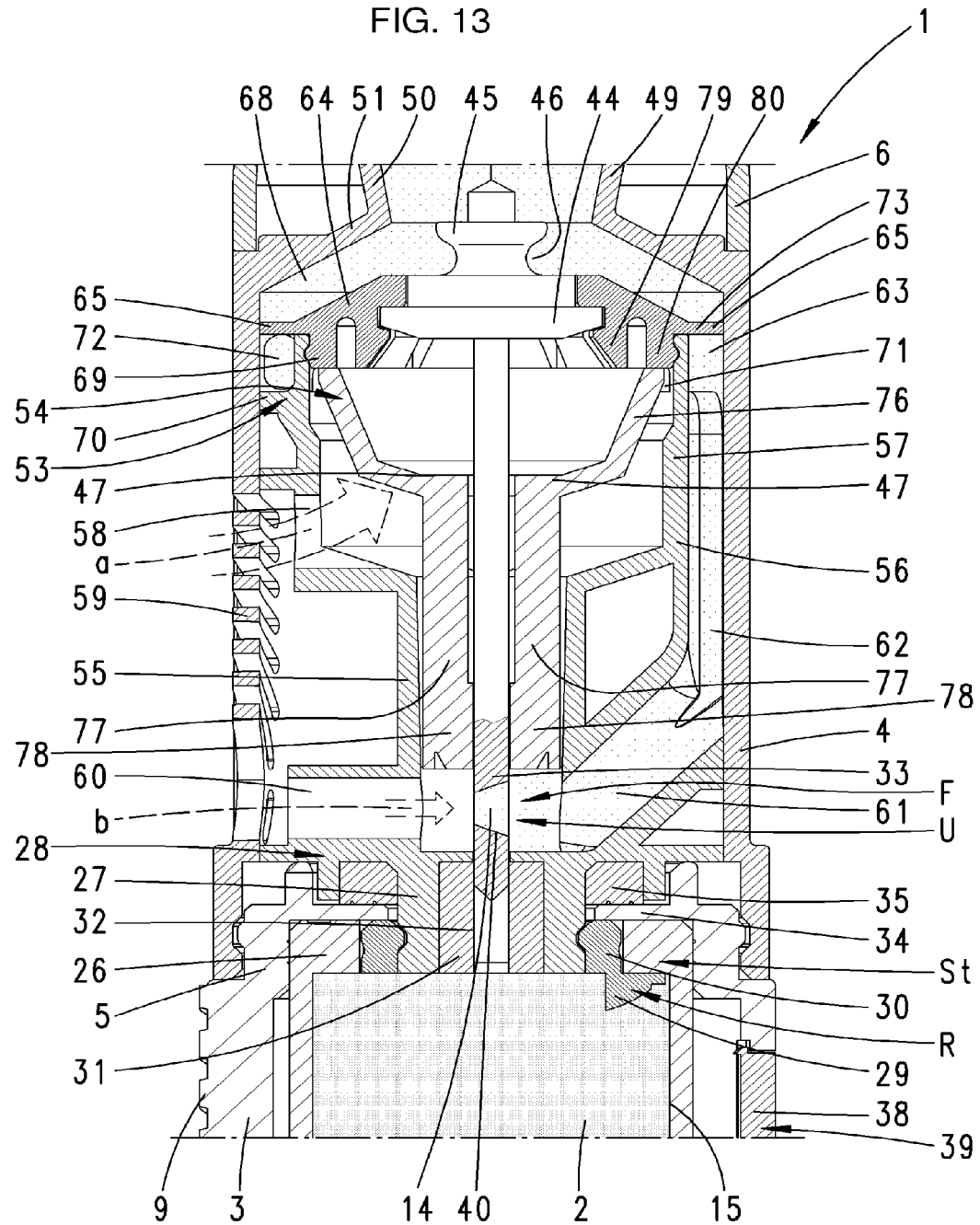
FIG. 13 shows a further detail-view illustration corresponding to FIG. 3, but relating to the situation according to FIG. 11.
Figure 14:
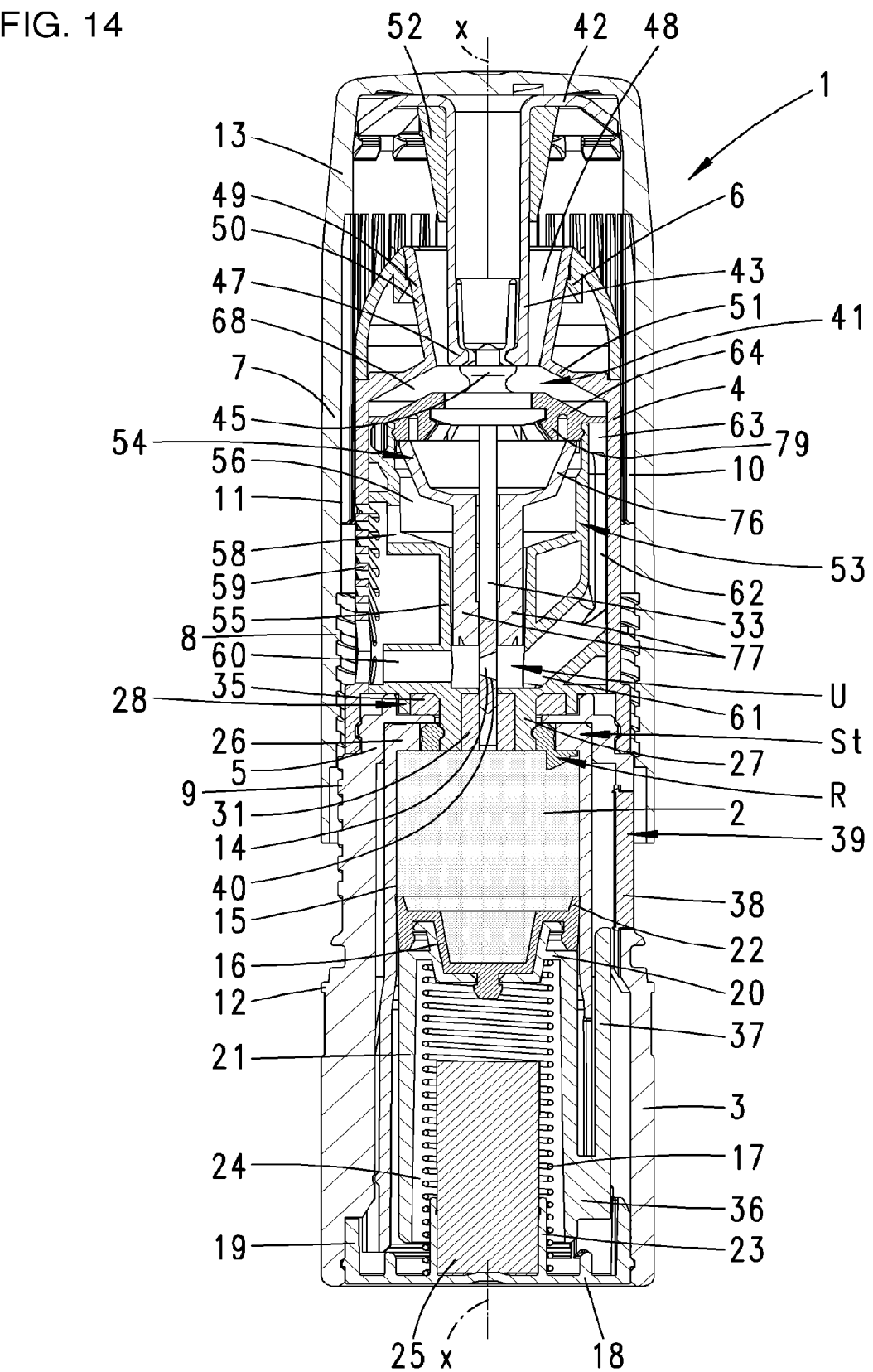
FIG. 14 shows a further vertical-section illustration corresponding to FIG. 1, this time relating to an intermediate position as the closure cap is being replaced following completion of inhalation.
Figure 15:
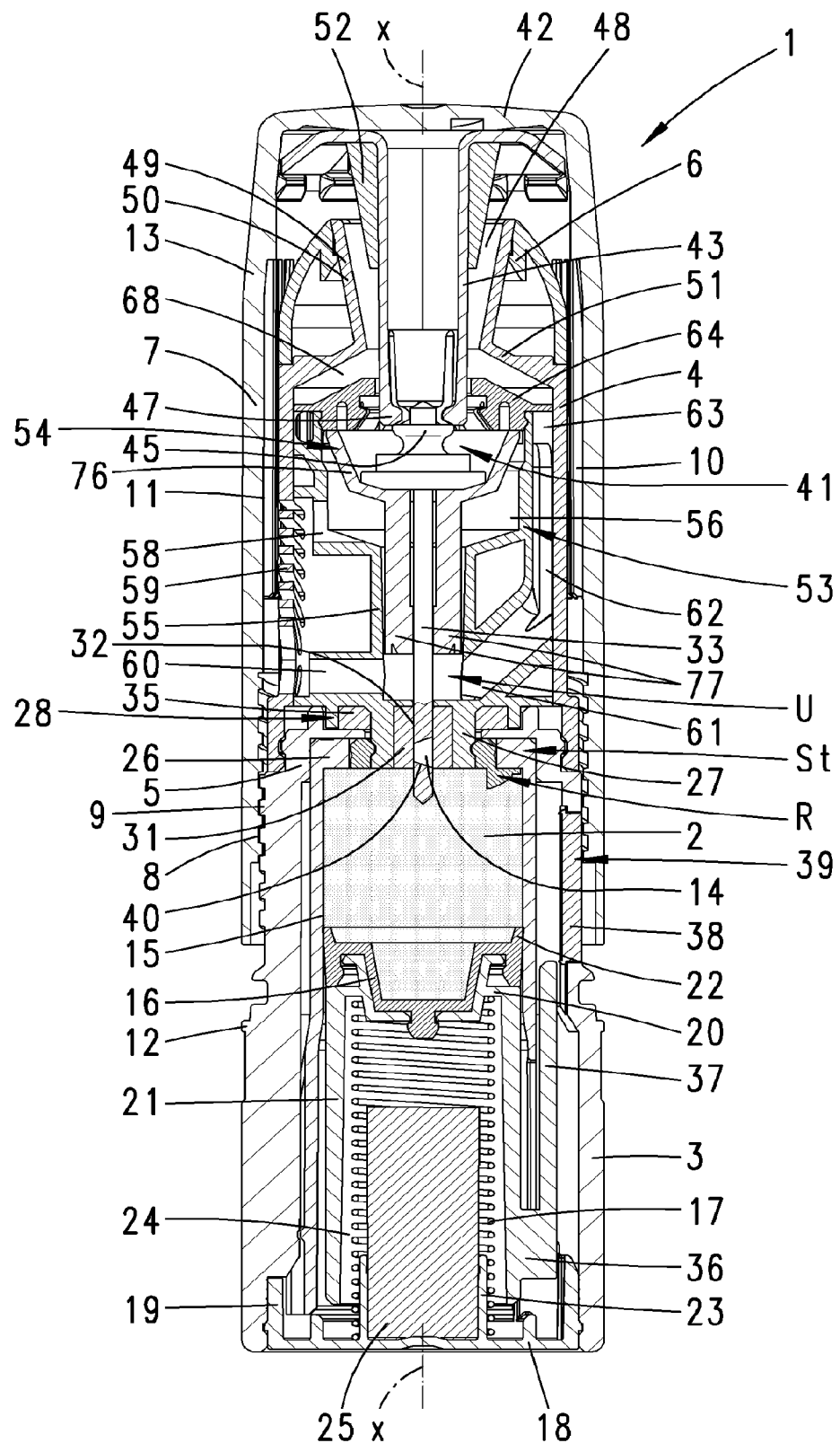
FIG. 15 shows a follow-up illustration to FIG. 14, relating to an intermediate position.
Figure 16:
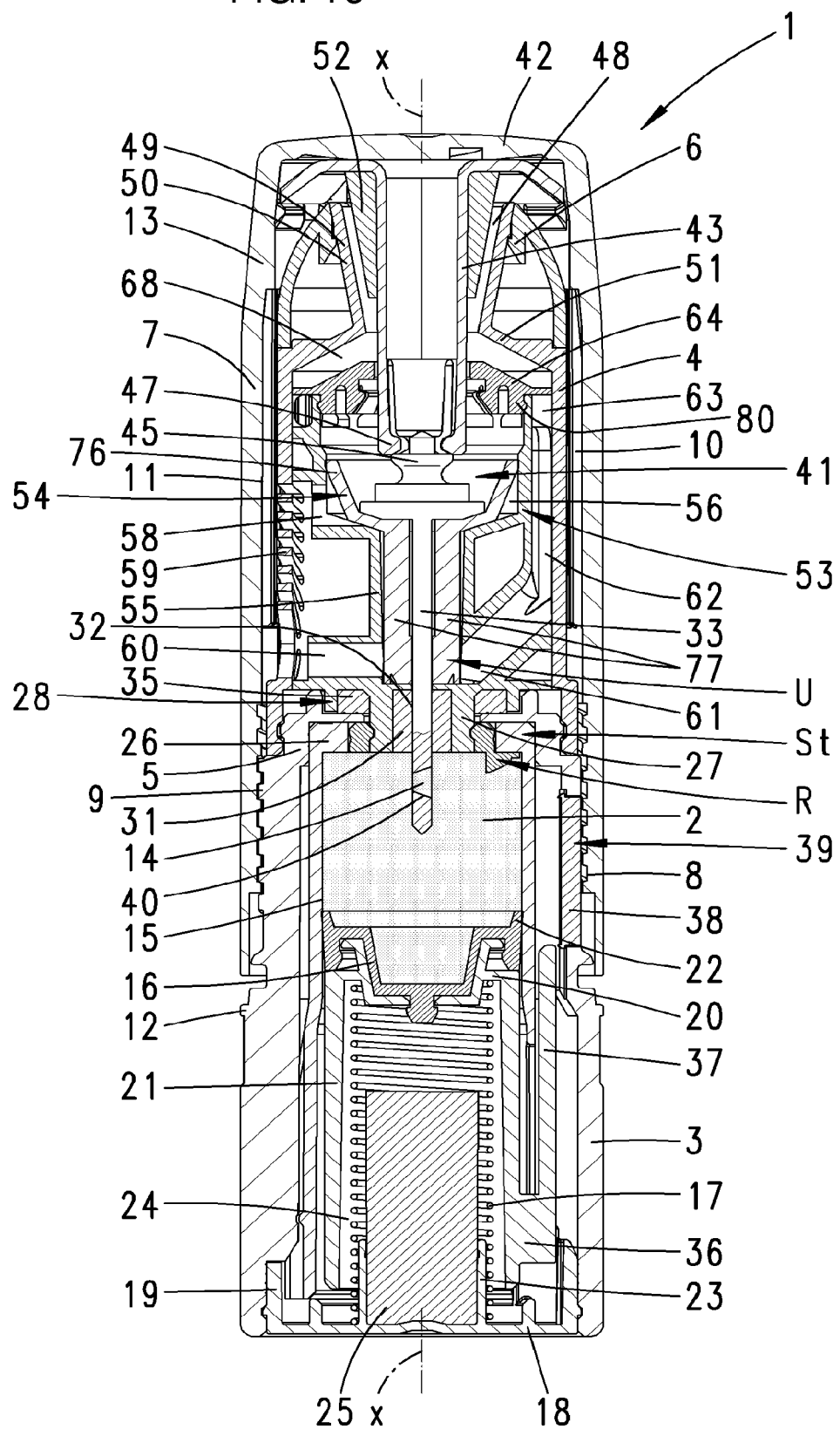
FIG. 16 shows a follow-up illustration to FIG. 15, relating to an intermediate position as the operation of screwing on the closure cap continues.
Figure 17:
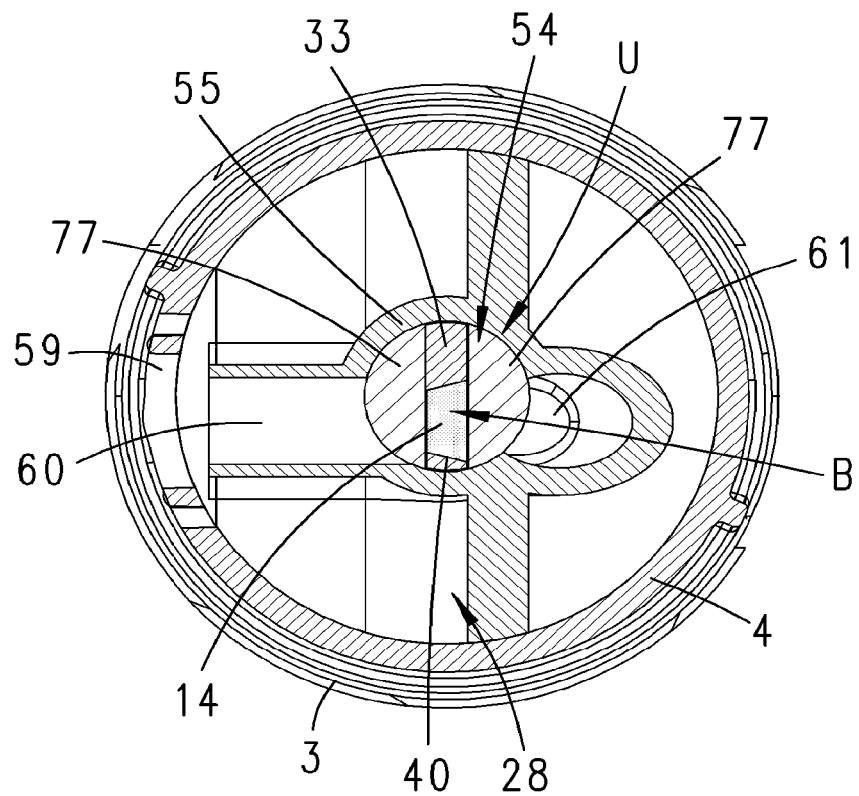
FIG. 17 shows the cross-section through the metering device in the emptying-standby position along line XVII-XVII in FIG. 8.

The device 1 cited functions as follows:

In order to prepare for inhalation, the closure cap 7 is first of all removed by unscrewing. As the closure cap 7 is being unscrewed upward, the coupling mentioned results in the outer cylinder 4 being carried along in rotation and, via this outer cylinder, the inner cylinder 53 as well as, in the exemplary embodiment cited, all those parts above the storage-chamber plane which are not connected in a rotationally fixed manner to the housing 3. Accordingly, the metering rod 33 is also carried along in rotation, and furthermore, the action of the closure cap 7 being unscrewed upward gives rise, at the same time, to axial displacement of the metering rod 33 via the docking location 41, which causes helical displacement of the metering chamber 40 into the as yet closed emptying-standby position B according to the illustration in FIGS. 6 and 7, in which it is aligned with the flow channel 60.

By virtue of the metering chamber 40 being disposed eccentrically in relation to the axis of rotation of the metering rod 33, it is filled optimally as a result of penetrating helically through the mass of substance, assisted by the rotor. The larger-diameter opening surface of the metering chamber 40 here is oriented in the direction of rotation.

The simultaneously rotating blade 29 of the rotor R here causes the surrounding mass of substance to be in a constantly loosened state, a shoveling effect being achieved. When the rotor R rotates in the opposite direction—as the closure cap 7 is screwed on again—the blade 29 interacts with the stator St in order to scrape off substance 2 from the surface of the stator and to press the substance 2 down, as a result of which the mass of substance is evened out. The blade 29 of the rotor R, accordingly, acts on the mass of substance in both directions of rotation.

When the removal-standby position B of the metering rod 33 is reached, the metering rod is secured with latching action. For this purpose, the radial collar 44 of the metering rod 33 moves behind latching fingers 79 which are formed on the underside of the ceiling 64.

As the screwing-action displacement of the closure cap 7 continues, the latching in the region of the docking location 41 between the hollow cylinder 43 and the metering rod 33 is eliminated. Accordingly, the noses 47 leave the annular groove 46, whereupon the closure cap 7 can be removed. The device 1 is now prepared for inhalation.

The screwing-action displacement of the closure cap 7 makes it possible to provide sufficient force for producing the latching between the radial collar 44 and latching fingers 79 and, furthermore, for eliminating the latching between the latching head 45 and noses 47 on the cap.

The tongues 77 of the piston 54 cover over the metering chamber 40 on each side. Accordingly, in this position, it is not possible for the sub-quantity 14 of substance to trickle out even in part. Rather, the substance is held reliably captive in the metering chamber 40. This prevents cases of double metering when inhalation is not carried out, but the device is closed-off again via the closure cap 7. Furthermore, in the removal-standby position B of the metering chamber 40, it is also possible for the device 1 to be put to one side. Even if the device 1 experiences normal kinds of impacts, this does not result in the sub-quantity 14 of substance which is to be inhaled trickling out, which would falsify the inhalation result.

The inhalation operation takes place automatically by the user subjecting the device to suction air, in the simplest case by the user breathing in.

Air is sucked in via the mouthpiece 6, and this, in first instance, by virtue of the piston head 76 being subjected to the action of air, results in the piston 54 being displaced axially in the direction of the ceiling 64. In the case of the exemplary embodiment illustrated, the pressure required to trigger the device is approximately 2 kgPa. Triggering takes place, as far as possible, in abrupt fashion.

In the raised position, the upper free peripheral region of the piston head 76 engages against the underside of an annular wall 80 of the ceiling 64. The annular space of the inner cylinder 53 which then encloses the free peripheral region of the piston head 76 is widened radially, as a result of which radial flow takes place around the piston 54 in the region of the piston head 76. This gives a main airstream a which flows through the grille-wall portion 59, passing through the radial openings 58, 58' and 58", into the piston-head displacement region 56 and passes, by way of the annular-space region left radially outside the piston head 76, through the openings 71 into the annular chamber 63. Approximately 85 to 90% of the total inhalation air volume is transported via this air-flow path.

At the same time, via the always open radial air-inlet openings 72, air is sucked in directly into the annular chamber 63, in order to predetermine the vortexing direction in the annular chamber 63.

By virtue of the axially displaced piston 54, the tongues 77 are likewise displaced axially, in order to release the metering chamber 40. The axial displacement of the piston 54 is assisted by the guide portion 55, which accommodates the tongues 77, widening slightly in the direction of the piston head 76, as a result of which there is a reduction in the friction between the tongues 77 and the wall of the guide portion 55. It is also the case that the friction between the tongues 44 and the flat part of the metering rod 33 is minimized, being on the region of the sealing surfaces 78.

The metering chamber 40 is then located in a removal-release position F, in which it lies freely in the flow path between the flow channel 60 and intermediate channel portion 61. In the exemplary embodiment illustrated, approximately 10 to 15% of the inhalation air volume is transported via this substance-transporting airstream b.

The metering chamber is cleared out with through-suction from the flow channel 60, this, furthermore, taking place from the smaller opening surface in the direction of the larger opening surface of the metering chamber 40. The two-fold deflection through in each case approximately 45° into the angled intermediate channel portion 61 and, from the latter, into the axially oriented channel 62 results, in the manner of a baffle-plate effect, in the initial breaking up of relatively large particles of powder, which further leads to an improved inhalation result.

The substance-laden airstream flowing axially, at relatively high speed, into the annular chamber 63 via the channel 62 is deflected via the deflecting-wall wing 73 and, assisted by the initial flow by way of the radial air-inlet openings 72, in the circumferential direction. Relatively large particles of powder are further broken up on this deflecting-wall wing 73.

As a result of this configuration, the substance-laden airstream is guided outside the piston region. The piston 54 merely has powder-free air flowing around it.

Optimum distribution of the sub-quantity 14 of substance which is to be inhaled is achieved in the annular chamber 63. The substance-laden air passes out through the intermediate spaces 67 for inhalation. Relatively heavy particles of powder which have possibly not been broken up, or have not been sufficiently broken up, are directed into the annular space 68 at the latest via the interrupter 74.

In the annular chamber 63, the initially substantially axially inflowing airstreams a and b are directed in a common horizontal direction of circulation in order then to pass jointly into the mouthpiece 6, with axial passage through the ceiling 64.

A number of features are provided in order to indicate successful inhalation to the user. In first instance, a visual check can be carried out in that the piston 54, once raised by suction air, is retained in its raised position on account of the, albeit low, frictional forces present. The piston 54, or the tongues 77 thereof, can be seen in the removal-standby position B through the radially outwardly open flow channel 60. This can be further assisted by the tongues 77 being conspicuously colored. Once inhalation has taken place and the piston 54 has been raised correspondingly, the tongues 77 cannot be seen. Rather, there is a free view of the empty metering chamber 40. It is also the case that the action of the piston 54 striking against the underside of the sealing 64 can be sensed both acoustically and by touch.

Once inhalation has taken place, and alternatively also if it is not desired to effect inhalation from the removal-standby position B, the closure cap 7 is screwed on again, the latching between the radial collar 44 and the latching fingers 79 being eliminated in first instance by virtue of the latching head 45 being acted upon by the noses 47. The retaining forces of this latching connection are of a correspondingly smaller magnitude than the amount of force which is necessary for deflecting the noses 47. As the action of screwing the closure cap 7 downward continues, the radial collar 44 on the metering rod displaces the piston 54 back again into its basic position. At the same time, with axial displacement and corresponding rotary movement, the metering rod 33 is displaced downward into the storage chamber. The action of the piston 54 being displaced back via the metering rod 33 terminates with the free ends of the tongues 77, which are formed in the manner of lips, striking against the facing ceiling surface of the cylinder part 27. As the downward-screwing displacement continues, finally the noses 47 enter into the annular groove 46 of the metering rod 33. This final latching action is discernable to the user acoustically and by touch, to indicate that the closing operation is at an end. It is thus also ensured that a latching action between the metering rod 33 and closure cap 7 which causes the metering rod 33, and thus the metering chamber 40, to be carried along into the removal-standby position B is only achieved in the lowermost position of the metering rod 33, in which position the metering chamber 40 is filled. Accordingly, there is always a filled metering chamber 40 available when the metering rod 33 is raised.

Incorrect operation is reliably avoided. Improper closure of the device 1 means that, during the next attempt at inhalation, the metering rod 33, which has accordingly not been raised, on the one hand closes the passage between the flow channel 60 and intermediate channel portion 61 by way of its flat-part portion. It is also the case that the metering rod 33 continues to act on the associated surface of the piston head 76 via the radial collar 44. Accordingly, when an attempt is made at inhalation, the closure of the flow channel 60 and the blocking of the piston 54 means that it is not possible to build up any air flow (with the exception of the small amount of flow via the small radial air-inlet openings 72). This clearly signals incorrect positioning to the user. This can only be eliminated by the device 1 being properly closed.

All features disclosed are (in themselves) pertinent to the invention. The disclosure content of the associated/attached priority documents (copy of the prior application) is hereby also included in full in the disclosure of the application, also for the purpose of incorporating features of these documents in claims of the present application.

LIST OF REFERENCE SIGNS

1 Device
2 Substance
3 Housing
4 Outer cylinder
5 Radial step
6 Mouthpiece
7 Closure cap
8 Internal thread
9 External thread
10 Ribs
11 Grooves
12 Annular shoulder
13 Actuating handle
14 Sub-quantity of substance
15 Storage chamber
16 Pressure-exerting base
17 Compression spring
18 Base cap
19 Latching collar
20 Inner shoulder
21 Hollow piston
22 Annular lip
23 Upright stub
24 Spring chamber
25 Drying-agent capsule
26 Chamber ceiling
27 Cylinder portion
28 Rotary part
29 Blade
30 Rotor ring
31 Sealing bushing
32 Guide opening
33 Metering rod
34 Housing portion
35 Annular seal
36 Radial extension arm
37 Indicating protrusion
38 Viewing window
39 Filling-level indicator

40 Metering chamber
41 Docking location
42 Closure-cap ceiling
43 Hollow cylinder
44 Radial collar
45 Latching head
46 Annular groove
47 Noses
48 Mouthpiece opening
49 Dispersing part
50 Wall
51 Ceiling portion
52 Drying-agent capsule
53 Inner cylinder
54 Piston
55 Guide portion
56 Piston-head displacement region
57 Region wall
58 Radial opening
58' Radial opening
58" Radial opening
59 Grille-wall portion
60 Flow channel
61 Intermediate channel portion
62 Channel
63 Annular chamber
64 Ceiling
65 Wing
66 Wing
67 Intermediate spaces
68 Annular space
69 Flange
70 Annular collar
71 Openings
72 Air-inlet openings
73 Deflecting-wall wing
74 Interrupter
75 Run-on slope
76 Piston head
77 Tongues
78 Sealing surfaces
79 Latching finger
80 Annular wall
x Device axis
B Removal-standby position
F Removal-release position
R Rotor
St Stator
U Transfer location
α Angle of intermediate spaces 67
β Angle of wings 66
δ Angle of wings 65
a Main airstream
b Substance-transporting airstream The invetion claimed is:

1. A metering device activated by a user induced airstream for an inhalation of a medicinal substance, the metering device comprising:
- a closure cap;
- a piston;
- a mouthpiece;
- an annular chamber disposed upstream of said mouthpiece;
- a storage chamber storing said medicinal substance which can be moved out of said storage chamber when said closure cap is removed;
- a metering rod comprising a metering chamber for removing said medicinal substance out of said storage chamber into an emptying-standby position,
  - in said emptying-standby position, said metering chamber being closed by said piston,
    - said piston being displaceable by said airstream into an emptying-release position,
  - in said emptying-release position, said metering chamber being released and said substance removed by said suction airstream; and
- wherein said piston comprises
  - a piston head and
  - two axially oriented tongues extending from an underside of said piston head, wherein along a lower free periphery, said tongues are split from one another.

2. The metering device according to claim 1, wherein said tongues along the lower free periphery, accommodate a cross-sectional contour of a guide portion of an inner cylinder.

3. The metering device according to claim 1, wherein along the lower free periphery, said tongues are configured split in a lip-like manner.

4. The metering device according to claim 1, wherein said pair of axially oriented tongues comprise a free peripheral region and said free peripheral regions comprise material-reinforced sealing surfaces.

5. The metering device according to claim 1, wherein said pair of axially oriented tongues are configured to help guide a flat part of said metering rod, wherein said flat part of said metering rod resides between said pair of axially oriented tongues having a stripping and sealing action.

6. A metering device activated by a user induced airstream for an inhalation of a medicinal substance, the metering device comprising:
- a closure cap;
- a piston;
- a mouthpiece;
- an annular chamber disposed upstream of said mouthpiece;
- a storage chamber storing said medicinal substance which can be moved out of said storage chamber when said closure cap is removed;
- a metering rod comprising a metering chamber for removing said medicinal substance out of said storage chamber into an emptying-standby position,
  - in said emptying-standby position, said metering chamber being closed by said piston,
    - said piston being displaceable by said airstream into an emptying-release position,
- in said emptying-release position, said metering chamber being released and said substance removed by said suction airstream;
- an outer cylinder; and
- a radially-oriented flow channel passing through the outer cylinder,
- wherein in said as yet closed emptying-standby position, said metering chamber is in axial alignment with the radially-oriented flow channel, in order to allow a visual check of said piston through the radially-oriented flow channel.

* * * * *